United States Patent
Keilsohn et al.

(10) Patent No.: US 12,384,935 B2
(45) Date of Patent: Aug. 12, 2025

(54) HYDROGELS FOR 3D PRINTING HAVING HIGH RESOLUTION

(71) Applicant: 3D SYSTEMS, INC., Rock Hill, SC (US)

(72) Inventors: Monica Keilsohn, San Diego, CA (US); Michael Brady, San Diego, CA (US); Khalil Moussa, Chapel Hill, NC (US)

(73) Assignee: 3D Systems, Inc., Rock Hill, SC (US)

(*) Notice: Subject to any disclaimer, the term of this patent is extended or adjusted under 35 U.S.C. 154(b) by 165 days.

(21) Appl. No.: 18/351,875

(22) Filed: Jul. 13, 2023

(65) Prior Publication Data

US 2024/0026183 A1    Jan. 25, 2024

Related U.S. Application Data

(60) Provisional application No. 63/408,554, filed on Sep. 21, 2022, provisional application No. 63/389,459, filed on Jul. 15, 2022.

(51) Int. Cl.

| | |
|---|---|
| *C09D 151/08* | (2006.01) |
| *A61L 27/16* | (2006.01) |
| *A61L 27/52* | (2006.01) |
| *B29C 64/124* | (2017.01) |
| *B29K 33/00* | (2006.01) |
| *B33Y 10/00* | (2015.01) |
| *B33Y 70/00* | (2020.01) |
| *C08F 290/06* | (2006.01) |
| *C09D 4/00* | (2006.01) |
| *C09D 7/41* | (2018.01) |

(52) U.S. Cl.
CPC ............ *C09D 151/08* (2013.01); *A61L 27/16* (2013.01); *A61L 27/52* (2013.01); *B33Y 70/00* (2014.12); *C08F 290/062* (2013.01); *C09D 4/00* (2013.01); *C09D 7/41* (2018.01); *A61L 2300/442* (2013.01); *B29C 64/124* (2017.08); *B29K 2033/08* (2013.01); *B33Y 10/00* (2014.12)

(58) Field of Classification Search
CPC .......... C09D 151/08; C09D 4/00; C09D 7/41; C09D 11/101; C09D 11/03; A61L 27/16; A61L 27/52; A61L 2300/442; B33Y 70/00; B33Y 10/00; B33Y 80/00; C08F 290/062; B29C 64/124; B29K 2033/08
See application file for complete search history.

(56) References Cited

U.S. PATENT DOCUMENTS

| | | |
|---|---|---|
| 2019/0136079 A1 | 5/2019 | Moussa |
| 2021/0229364 A1* | 7/2021 | McLeod ............... B33Y 50/02 |
| 2023/0256668 A1* | 8/2023 | Nishida ................ B33Y 40/00 |
| | | 264/401 |

FOREIGN PATENT DOCUMENTS

| | | |
|---|---|---|
| CN | 108948379 A | 12/2018 |
| CN | 109880024 A | 6/2019 |
| CN | 112111073 A | 12/2020 |
| WO | 2022236061 A1 | 11/2022 |
| WO | 2023049137 A1 | 3/2023 |

OTHER PUBLICATIONS

PCT International Search Report for International Search Authority for PCT/US2023/070141 mailed Oct. 24, 2023 (6 pages).
PCT International Written Opinion for International Search Authority for PCT/US2023/070141 mailed Oct. 24, 2023 (7 pages).
Jieping Wang et al: "A highly efficient waterborne photoinitiator for visible-light-induced three-dimensional printing of hydrogels", Chemical Communications, vol. 54, No. 8, Jan. 1, 2018 (Jan. 1, 2018), pp. 920-923, XP055737100, UK; ISSN: 1359-7345, DOI: 10.1039/C7cC09313F p. 922, left-hand column, paragraph 2—& Wang Jieping et al: "A highly efficient waterborne photoinitiator for visible-light-induced three-dimensional printing of hydrogels", Jan. 1, 2018 (Jan. 1, 2018), XP093091298, Retrieved from the Internet: URL: https://www.rsc.org/suppdata/c7/cc/c7cc09313f/...cc09313f/.
EPO translation of CN 108948379A @TXPMTCEA on Oct. 18, 2023 (8 pages).
EPO translation of CN 1112111073A @TXPMTCEA on Oct. 18, 2023 (19 pages).
EPO translation of CN 109880024A @TXPMTCEA on Oct. 18, 2023 (12 pages).

* cited by examiner

*Primary Examiner* — Nahida Sultana
(74) *Attorney, Agent, or Firm* — Maynard Nexsen PC; John P. Zimmer

(57) ABSTRACT

In one aspect, build materials for use with a three-dimensional (3D) printing system are described herein. In some embodiments, a build material described herein comprises an acrylate component, a photoinitiator component, a non-curable absorber component, and water. The photoinitiator component of the build material is operable to initiate curing of the acrylate component and/or other curable materials that may optionally be present when the photoinitiator is exposed to incident curing radiation having a Gaussian distribution of wavelengths and a peak wavelength $\lambda$. The build material has a penetration depth ($D_p$) and a critical energy ($E_c$) at the wavelength $\lambda$. In some embodiments, the $D_p$ is greater than 200 μm and less than 300 μm, and the $E_c$ is 3-12 mJ/cm². In other embodiments, the $D_p$ is greater than 10 μm and less than 50 μm, and the $E_c$ is 5-40 mJ/cm².

20 Claims, No Drawings

HYDROGELS FOR 3D PRINTING HAVING HIGH RESOLUTION

CROSS REFERENCE TO RELATED APPLICATIONS

This application claims priority pursuant to 35 U.S.C. § 119 to U.S. Provisional Patent Application No. 63/389,459, filed Jul. 15, 2022, and to U.S. Provisional Patent Application No. 63/408,554, filed Sep. 21, 2022, each of which is hereby incorporated by reference in its entirety.

FIELD

The present invention relates to methods of three-dimensional (3D) printing and build materials for use with 3D printing systems and, more particularly, to build materials for 3D printing hydrogel objects with desired resolution.

BACKGROUND

Additive manufacturing systems or 3D printers use build materials, which can also be referred to as inks or polymerizable liquids in some cases, to form various objects, articles, or parts in accordance with computer generated files. In some instances, the build material is solid at ambient temperatures and converts to liquid at elevated jetting temperatures. In other instances, the build material is liquid at ambient temperatures. Build materials can be formed into 3D objects in various manners, such as by jetting or otherwise depositing the build material onto a substrate. Build materials can also be selectively cured, solidified, or otherwise altered during a build. For example, some 3D printers form 3D articles from a reservoir, vat, or container of a fluid build material or a powdered build material. In some cases, a binder material or a laser or other source is used to selectively solidify or consolidate layers of the build material in a stepwise fashion to provide the 3D article.

In 3D printing systems using curing radiation, the curing radiation can penetrate deeper into the build material than intended or desired. More specifically, the radiation can penetrate deeper than the portion of build material that is intended to be cured or consolidated as part of the printed article structure. Such an undesired, excess cure depth can be referred to as "print through" or "print through depth." The occurrence of print through can be problematic for a number of reasons. First, print through can result in the formation of an undesired "gummy" layer of partially cured build material on certain surfaces of an additive manufacturing system (such as one or more "down surfaces"). Second, print through wastes build material. Third, even at its most benign, print through generally requires compensation in the build process to take into account that some layer or other of the printed article will be different than intended (e.g., different than a corresponding computer aided design or "CAD" file dictates). For example, such deviations can sometimes be accounted or compensated for when creating or selecting a specific CAD file to be used to form a printed article. However, such compensation may not be accurate, leading to part distortion and general loss of printing accuracy. Finally, the occurrence of print through generally introduces a greater number of unknown or imprecise values into a build process. Moreover, the greater the print through, the greater the introduction of error and/or uncertainty. Such uncertainty is of course undesired in an additive manufacturing process.

There exists a need for improved methods and, more particularly, for improved build materials for 3D printing that have improved printing properties, including but not limited to in relation to depth of penetration of light or print through properties. There is a special need for improved build materials that can be used to form biomaterials, such as hydrogel implants serving as scaffolds for tissue regeneration and/or various cellular therapies, including at a desired printing resolution.

SUMMARY

In one aspect, build materials for use with a 3D printer are described herein, which, in some embodiments, may offer one or more advantages over prior build materials, particularly radiation-curable build materials for use in additive manufacturing. For reference purposes herein in the context of additive manufacturing, the term "build material" (or its plural) can be used interchangeably with the term "ink" or "polymerizable liquid" (or their plurals). In some embodiments, a build material described herein can be used to print hydrogel articles with improved accuracy and/or precision. Build materials described herein, in some cases, also provide improved resolution without sacrificing speed of the additive manufacturing process, without sacrificing energy efficiency of the additive manufacturing process, and/or without sacrificing desired mechanical properties of the printed articles. Moreover, build materials described herein can be used in a variety of different 3D printers or additive manufacturing systems, such as those based on Stereolithography (SLA), Digital Light Processing (DLP), and Multi-Jet Printing (MJP).

In some embodiments, a build material for use in a 3D printing system described herein comprises an acrylate component, a photoinitiator component, a non-curable absorber component, and water. Moreover, in some cases, one or more additional curable materials may optionally be present in the build material, in addition to the acrylate component. Additional non-curable components may also be present in some embodiments. It is to be understood, of course, that the total amount, or sum of the amounts, of the acrylate component, the photoinitiator component, the non-curable absorber component, the additional curable material component (if present), the additional non-curable material component (if present), and the water is equal to 100 weight percent (wt. %). In addition, the additional non-curable components may include a colorant, an inhibitor, and/or a stabilizing agent.

Further, the photoinitiator component of the build material is operable to initiate curing of the acrylate component (and/or to initiate curing of other curable materials that may optionally be present) when the photoinitiator component is exposed to incident curing radiation having a Gaussian distribution of wavelengths and a peak wavelength $\lambda$. Moreover, the build material has a penetration depth ($D_p$) and a critical energy ($E_c$) at the wavelength $\lambda$. The terms $D_p$ and $E_c$ are described in further detail below. In some preferred embodiments, the $D_p$ of the build material is greater than 200 µm and less than 300 µm. Additionally, in some such cases, the $E_c$ is 3-12 mJ/cm$^2$. Alternatively, in other preferred embodiments, the $D_p$ is greater than 10 µm and less than 50 µm (e.g., 15-25 µm). Further, in some such instances, the $E_c$ is 5-40 mJ/cm$^2$ or 10-40 mJ/cm$^2$. In still other preferred embodiments, the $D_p$ is greater than 25 µm and less than 50 µm. Additionally, in some such instances, the $E_c$ is 5-30 mJ/cm$^2$. Build materials having such properties can provide various advantages, including improved resolution and/or printing speed in some instances.

As described further below, the amounts of photoinitiator and/or non-curable absorber material included in a build material can be selected to obtain a desired $D_p$, $E_c$, and/or $D_{PT}$ value, in combination with other components of the build material (the terms $D_p$, $E_c$, and $D_{PT}$, which refers to the print through depth of the build material, are described further below). In some embodiments, for example, a build material described herein comprises up to 5 wt. %, up to 3 wt. %, or up to 2 wt. % photoinitiator component, and up to 2 wt. %, up to 1.5 wt. %, or up to 1 wt. % non-curable absorber component, based on the total weight of the build material. Additionally, in some instances, the total absorbance of the non-curable absorber component at the wavelength λ is about 0.1 to 10 times the total absorbance of the photoinitiator component at the wavelength λ. Further, in some cases, both the non-curable absorber component and the photoinitiator component of a build material described herein have an absorption peak within 30 nm of the wavelength λ.

In another aspect, methods of forming a 3D article by additive manufacturing are described herein. In some embodiments, such a method comprises providing a build material described herein and selectively curing a portion of the build material using incident curing radiation having a Gaussian distribution of wavelengths and a peak wavelength at the wavelength λ. For example, in some instances, the build material has a $D_p$ greater than 200 μm and less than 300 μm, and an $E_c$ of 3-12 mJ/cm². In other embodiments, the $D_p$ is greater than 10 μm and less than 50 μm (e.g., 15-25 μm), and the $E_c$ is 5-40 mJ/cm² or 10-40 mJ/cm². In still other embodiments, the $D_p$ is greater than 25 μm and less than 50 μm, and the $E_c$ is 5-30 mJ/cm². Additionally, in some embodiments of a method described herein, the build material is selectively cured according to preselected computer aided design (CAD) parameters, and the $D_p$ corresponds to a voxel depth of the CAD parameters.

Moreover, in some cases, providing the build material comprises selectively depositing layers of the build material in a fluid state onto a substrate to form the three-dimensional article. Alternatively, in other embodiments, providing the build material comprises retaining the build material in a fluid state in a container, and selectively curing a portion of the build material comprises selectively applying the curing radiation to the build material in the container to solidify or consolidate at least a portion of a first fluid layer of the build material, thereby forming a first solidified or consolidated layer that defines a first cross-section of the article. Such a method may also further comprise raising or lowering the first solidified layer to provide a second fluid layer of the build material at a surface of the fluid build material in the container, and selectively applying the curing radiation to the build material in the container to solidify at least a portion of the second fluid layer of the build material, thereby forming a second solidified layer that defines a second cross-section of the article, the first cross-section and the second cross-section being bonded to one another in a z-direction. As described further hereinbelow, the foregoing steps may be repeated any desired number of times needed to complete the 3D article.

In still another aspect, printed 3D articles are described herein. Such a printed 3D article can be formed from any build material and using any method described herein. Such printed 3D articles, in some cases, have superior accuracy compared to some other 3D articles.

These and other embodiments are described in greater detail in the detailed description which follows.

DETAILED DESCRIPTION

Embodiments described herein can be understood more readily by reference to the following detailed description and examples. Elements, apparatus and methods described herein, however, are not limited to the specific embodiments presented in the detailed description and examples. It should be recognized that these embodiments are merely illustrative of the principles of the present disclosure. Numerous modifications and adaptations will be readily apparent to those of skill in the art without departing from the spirit and scope of the disclosure.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, 1 to 4, 3 to 7, 4.7 to 10.0, 3.6 to 7.9, or 5 to 8.

All ranges disclosed herein are also to be considered to include the end points of the range, unless expressly stated otherwise. For example, a range of "between 5 and 10," "from 5 to 10," or "5-10" should generally be considered to include the end points 5 and 10.

Further, when the phrase "up to" is used in connection with an amount or quantity, it is to be understood that the amount is at least a detectable amount or quantity (that is, the amount is a non-zero amount). For example, a material present in an amount "up to" a specified amount can be present from a detectable (or non-zero) amount and up to and including the specified amount.

It is also to be understood that the article "a" or "an" refers to "at least one," unless the context of a particular use requires otherwise.

The terms "three-dimensional printing system," "three-dimensional printer," "printing," and the like generally describe various solid freeform fabrication techniques for making three-dimensional articles or objects by stereolithography, selective deposition, jetting, fused deposition modeling, multi-jet modeling, and other additive manufacturing techniques now known in the art or that may be known in the future that use a build material to fabricate three-dimensional objects.

I. Build Materials for 3D Printing

In one aspect, build materials for use with a 3D printer are described herein. In some embodiments, a build material described herein comprises an acrylate component, a photoinitiator component, a non-curable absorber component, and water. Other components, such as one or more additional curable materials or one or more additional non-curable materials, may also be included in a build material described herein. Further, the photoinitiator component is operable to initiate curing of the acrylate component (and, optionally, other curable materials present) when the photoinitiator component is exposed to incident curing radiation having a Gaussian distribution of wavelengths and a peak wavelength λ. That is, the photoinitiator component is a photoinitiator of curing of the acrylate component and/or other curable materials present in the build material. Additionally, the build material has a penetration depth ($D_p$) and a critical energy ($E_c$) at the wavelength λ.

A build material described herein may also have a print through depth ($D_{PT}$) corresponding to the $D_p$ and/or $E_c$. As understood by one of ordinary skill in the art, $D_{PT}$ refers to the total cure depth minus layer thickness, where the "total cure depth" refers to the depth at which any curing or polymerization of the build material occurs in response to the incident curing radiation. "Layer thickness" refers to the thickness of the region in which "full" curing or polymerization of the build material occurs in response to the incident curing radiation. Such "full" curing refers to the maximum curing provided by the incident radiation. For example, in some cases, "full" curing corresponds to 80-100% curing, 80-95% curing, 80-90% curing, 85-100% curing, 85-99% curing, 85-95% curing, 90-100% curing, 90-99% curing, or 90-95% curing, where the percentage is based on the total number of available curable moieties.

The degree or percentage of curing (or polymerization) can be determined using any protocol or method not inconsistent with the technical objectives of the present disclosure, such as by determining the percentage of monomers (or curable moieties) incorporated into the polymer network (e.g., based on molecular weight of the polymer compared to the molecular weight of the monomer, or based on the total polymer mass compared to the theoretical maximum of the total polymer mass) or by determining the amount of unincorporated monomers or unreacted curable moieties. When more than one method is used to determine a degree of curing or polymerization, the results of the methods can be averaged to obtain a percentage described herein. It is further to be understood that the degree of curing or polymerization described herein is different than "degree of polymerization" defined as the number of repeating units in a polymer molecule.

It is to be understood that the parameters or properties $D_p$, $E_c$, and $D_{PT}$ are structural parameters or properties of a build material described herein. A discussion of the "structural" or "compositional" nature of these values can be found, for instance, in Chapter 4 of Paul F. Jacobs, *Rapid Prototyping & Manufacturing: Fundamentals of Stereolithography* (Society of Manufacturing Engineers, McGraw-Hill, 1992) (first edition) (hereinafter referred to as "Jacobs"). As understood by one of ordinary skill in the art, the value $D_p$ is the penetration depth of the build material, defined as that depth of the build material which results in a reduction of the irradiance to a level equal to 1/e of the surface irradiance, where e is the base of natural logarithms (equal to 2.7182818 . . . ). $E_c$ is the critical energy, which is the energy needed to obtain the gel point of a build material, as described on page 86 of Jacobs. Moreover, as further described by Jacobs (pages 86-89), the metric $E_c$ is equal to the intercept of a working curve corresponding to a semilog plot of cure depth on the ordinate and the logarithm of maximum radiation exposure on the abscissa. $E_c$ is assigned to the intercept, at which the cure depth is zero. Reference can also be made to "Fundamentals of Stereolithography" by Dr. Paul F. Jacobs in the Proceedings of the 1992 International Solid Freeform Fabrication Symposium held in Austin, Texas, USA (pages 196-211).

It is further to be understood that the amounts of photoinitiator component and/or non-curable absorber component included in a build material described herein can be selected to obtain a desired $D_p$, $E_c$, and/or $D_{PT}$ value, in combination with other components of the build material. However, it is to be understood that, in some instances, the other components of the build material, such as the acrylate component, can vary in type and/or in quantity without substantially changing the desired $D_p$, $E_c$, and/or $D_{PT}$ values obtained by the particular combination of photoinitiator component and/or non-curable absorber component. For instance, in some cases, changes in the type and/or quantity of the acrylate component (within the scope of the presently disclosed types and quantities) affect the $D_p$, $E_c$, and/or $D_{PT}$ values of a build material by 5% or less, 4% or less, 3% or less, 2% or less, or 1% or less. More particularly, such minimal changes in the $D_p$, $E_c$, and/or $D_{PT}$ values can be obtained when the components of the build material other than the photoinitiator component and non-curable absorber component (such as the acrylate component) do not absorb (or refract or reflect) or only minimally absorb (or refract or reflect) light of the wavelength λ. Alternatively, such minimal changes in the $D_p$, $E_c$, and/or $D_{PT}$ values can also be obtained when the components of the build material other than the photoinitiator component and non-curable absorber material component (such as the acrylate component) absorb (or refract or reflect) light of the wavelength λ to approximately the same degree, no matter which precise species or amounts of components are selected (within the confines of the presently disclosed options for species and amounts). In other words, in the context of compositions and methods described herein, the components of build materials described herein, other than the photoinitiator component and non-curable absorber component, can essentially be (and generally are) optical "spectator" species at the wavelength λ, such that these "spectator" species do not substantially affect the $D_p$, $E_c$, and/or $D_{PT}$ values of the overall build material. Thus, as described in more detail below, the acrylate component or other curable component can, in some instances, be varied as desired from build material to build material (in terms of precise species and/or quantity) such that the precise species and/or quantity used from build material to build material have similar optical absorption profiles and/or refractive indices.

Moreover, in some cases, a build material described herein has a $D_p$ value and an $E_c$ value at the wavelength λ that correspond to desired optical and chemical characteristics or performance metrics of the build material. It is also possible for build materials having certain $D_p$ and $E_c$ values or ranges of values to define a "regime" that is especially desirable for certain end use applications of the build material. For example, in some embodiments, $D_p$ and $E_c$ values of a build material or "family" of build materials are selected based on a power and/or wavelength of a source of curing radiation desired to be used with the build material, based on a desired voxel size or voxel depth of a CAD profile desired to be used with the build material, based on a desired feature resolution of the printed article formed from the build material, and/or based on a desired printing speed to be used with the build material.

In one "regime," for instance, the $D_p$ of the build material is greater than 200 μm and less than 300 μm, and the $E_c$ of the build material is 3-12 mJ/cm². Additionally, in some such cases, a build material described herein has a ratio of $D_p$ to $E_c$, in units of (μm cm²)/mJ, of greater than 10 or greater than 15. In some embodiments, the build material has a ratio of $D_p$ to $E_c$, in units of (μm cm²)/mJ, between 15 and 100, between 15 and 50, between 15 and 25, or between 20 and 50. Such $D_p$, $E_c$, and $D_p/E_c$ values can provide desirable performance as described above, such as when a desired voxel size is greater than 50 μm per side on average (e.g., when a desired voxel size corresponds to a volume having an average length in all three dimensions of 50-100 μm, 50-75 μm, 60-100 μm, 60-80 μm, or 60-70 μm).

In other exemplary embodiments, the $D_p$ of the build material is greater than 10 μm and less than 50 μm (for example, in some such cases, the $D_p$ is 15-25 μm), and the $E_c$ is 5-40 mJ/cm², 10-40 mJ/cm², or 5-35 mJ/cm². Further, in some such instances, a build material described herein has a ratio of $D_p$ to $E_c$, in units of (μm cm²)/mJ, of less than 5, less than 3, less than 2, less than 1.5, or less than 1. For example, in some implementations, a build material described herein has a ratio of $D_p$ to $E_c$, in units of (μm cm²)/mJ, of 0.2 to 2, 0.3 to 1.5, 0.5 to 1.5, or 1 to 2. Such $D_p$, $E_c$, and $D_p/E_c$ values can provide desirable performance as described above, such as when a desired voxel size is less than 100 μm, less than 70 μm, less than 50 μm, less than 40 μm, or less than 30 μm per side on average (e.g., when a desired voxel size corresponds to a volume having an average length in all three dimensions of 10-100 μm, 10-45 μm, 10-40 μm, 10-30 μm, 15-45 μm, 15-40 μm, or 15-25 μm).

In still other exemplary embodiments, the $D_p$ of the build material is greater than 25 μm and less than 50 μm, and the $E_c$ is 5-30 mJ/cm² or 5-10 mJ/cm². Further, in some such instances, a build material described herein has a ratio of $D_p$ to $E_c$, in units of (μm cm²)/mJ, of less than 10, such as a ratio between 2 and 6, or between 3 and 5. Such $D_p$, $E_c$, and $D_p/E_c$ values can provide desirable performance as described above, such as when a desired voxel size is less than 50 μm, less than 40 μm, or less than 30 μm per side on average (e.g., when a desired voxel size corresponds to a volume having an average length in all three dimensions of 10-45 μm, 10-40 μm, 10-30 μm, 15-45 μm, or 15-40 μm).

In addition to $D_p$, $E_c$, and $D_p/E_c$ values described above for one regime or another, a build material described herein can also have a desired or beneficial $D_{PT}$ value. For example, in some cases, a build material described herein has a $D_{PT}$ at the wavelength λ of less than or equal to 1.5×$D_p$, less than or equal to 1.3×$D_p$, less than or equal to 1.2×$D_p$, or less than or equal to 1.1×$D_p$. In some instances, the $D_{PT}$ at the wavelength λ is between 0.8× and 2×$D_p$, between 0.8× and 1.5×$D_p$, between 0.9× and 2×$D_p$, between 0.9× and 1.8×$D_p$, between 0.9× and 1.5×$D_p$, between 0.9× and 1.3×$D_p$, between 1× and 2×$D_p$, between 1× and 1.7×$D_p$, between 0.1× and 1.5×$D_p$, between 1.1× and 2×$D_p$, between 1.1× and 1.5×$D_p$, between 1.2× and 2×$D_p$, between 1.2× and 1.8×$D_p$, between 1.3× and 2×$D_p$, between 1.3× and 1.7×$D_p$, or between 1.5× and 2×$D_p$.

Not intending to be bound by theory, it is believed that a build material having such a combination of $D_p$, $E_c$, and $D_p/E_c$, and optionally $D_{PT}$ provides improved consistency, accuracy, and resolution when used as a build material in an additive manufacturing process, including an additive manufacturing process described herein for particular end uses.

A "non-curable absorber" component or material, for reference purposes herein, is a material or chemical species that is not curable or substantially curable by the curing radiation described herein and that absorbs at least a portion of the curing radiation, without causing substantial curing of other components of the build material. Thus, a "non-curable" absorber component or material can also be referred to as a "non-curing" or "non-reactive" absorber component or material. Moreover, a non-curable or non-curing absorber component described herein that is not "substantially" curable or that does not cause "substantial" curing is understood to convert (or use) less than 5%, less than 1%, less than 0.5%, or less than 0.1% of absorbed curing radiation photons into (or in) a curing event. For example, a non-curable (or non-curing) absorber component or material described herein, in some embodiments, can convert less than 2%, less than 1%, less than 0.5%, or less than 0.1% of absorbed photons into a free-radical species that can initiate or participate in (meth)acrylate polymerization or another curing process.

It is further to be understood that a non-curable or non-curing absorber component or material described herein can be a polymerization "spectator" (i.e., non-polymerizing or non-polymerization-initiating) species that nevertheless "competes" with a photoinitiator component of the build material for absorption of photons of incident curing radiation. Thus, in some cases, a non-curable absorber component and a photoinitiator component of a build material described herein have substantially overlapping photon absorption profiles, particularly in a region of the electromagnetic spectrum corresponding to or including the peak wavelength λ described above. In some instances, for example, both the non-curable absorber component and the photoinitiator component have an absorption peak within 30 nm, within 20 nm, within 15 nm, within 10 nm, or within 5 nm of the wavelength λ.

However, it is to be understood that a non-curable absorber component and a photoinitiator component of a build material described herein need not have the same absorbance, optical density, extenuation coefficient, and/or molar extinction coefficient at the wavelength λ or at any other specific wavelength. Instead, the non-curable absorber component and the photoinitiator component can have differing absorbances, optical densities, extenuation coefficients, and/or molar extinction coefficients at the wavelength λ, as well as at other wavelengths.

In addition, in some cases, the amount of photoinitiator component and the amount of non-curable absorber component included in a build material described herein are selected based on similarities or differences between the absorbances, optical densities, extenuation coefficients, and/or molar extinction coefficients of the species, including at the wavelength λ. For instance, in some cases, the amounts of the photoinitiator component and the non-curable absorber component are selected to provide a desired ratio of total absorbance of each species at the wavelength λ, and/or to provide a desired $D_{PT}$, $D_p$, $E_c$, or $D_p/E_c$ value described hereinabove. In some such embodiments, the total absorbance of the non-curable absorber component at the wavelength λ is about 0.1 to 10 times, about 0.2 to 5 times, or about 0.5 to 2 times the total absorbance of the photoinitiator component at the wavelength λ, where the "total absorbance" of each species or component at the wavelength λ is understood to refer to the amount (in moles) of the species or component times the molar extinction coefficient of the species or component at the wavelength λ.

It should further be noted that the wavelength λ can be any wavelength not inconsistent with the objectives of the present disclosure. For example, in some cases, λ is a wavelength in the ultraviolet (UV) or visible region of the electromagnetic spectrum. In some cases, the peak wavelength λ is in the infrared (IR) region of the electromagnetic spectrum. In some embodiments, the wavelength λ is between 250 nm and 400 nm, between 300 nm and 385 nm, or between 385 nm and 405 nm. In other cases, the wavelength λ is between 600 nm and 800 nm or between 900 nm and 1.3 μm. However, the precise wavelength λ is not particularly limited. Moreover, in some cases, the photoinitiator component and/or non-curable absorber component of a build material described herein has an absorption peak within a wavelength range above, such as between 300 nm and 385 nm or between 385 nm and 405 nm.

Any non-curable absorber material or component not inconsistent with the technical objectives of the present disclosure may be used in a build material described herein. For example, in some embodiments, a non-curable absorber component comprises a "dye" that has an absorption profile consistent with the description above. Such a "dye" may, more particularly, be a hydrophilic or water-soluble dye, in some cases. For instance, in some implementations, the non-curable absorber component comprises a water-soluble yellow dye. A water-soluble blue dye or green dye may also be used.

In some embodiments, the non-curable absorber component of a build material described herein comprises a quinoline yellow or a sulfonated quinoline yellow. In some instances, the sulfonated quinoline yellow comprises at least one of monosulfonate, disulfonate and trisulfonate species.

Additionally, in some cases, the sulfonated quinoline yellow can be of Formula I:

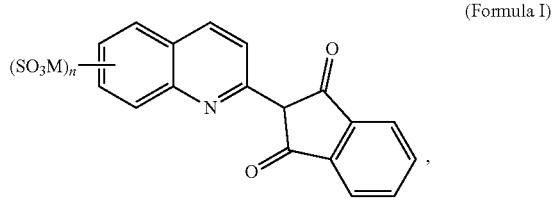

(Formula I)

wherein M is sodium or hydrogen and the subscript n is an integer from 1 to 3. It is further to be understood that Formula I above can have resonance structures or other structures with which it is in equilibrium. Formula I above can be understood as representing such structures also.

Additionally, in some cases, the non-curable absorber component of a build material described herein comprises tartrazine. In some embodiments, the non-curable absorber component comprises UV386A (commercially available from QCR Solutions). Other non-curable absorber materials may also be used.

The non-curable absorber component can be present in a build material described herein in any amount not inconsistent with the technical objectives of the present invention. In some embodiments, for example, the non-curable absorber component is present in a build material in an amount up to 10 wt. % or up to 5 wt. %, based on the total weight of the build material. For example, in some instances, a build material comprises up to 3 wt. %, up to 2 wt. %, up to 1.5 wt. %, or up to 1 wt. % non-curable absorber material. In some embodiments, a build material comprises 0.01-10 wt. %, 0.01-5 wt. %, 0.01-3 wt. %, 0.01-2 wt. %, 0.01-1 wt. %, 0.05-10 wt. %, 0.05-5 wt. %, 0.05-3 wt. %, 0.05-1 wt. %, 0.1-10 wt. %, 0.1-7 wt. %, 0.1-5 wt. %, 0.1-3 wt. %, 0.1-2 wt. %, 0.1-1 wt. %, 0.1-0.5 wt. %, 0.2-1 wt. %, 0.2-0.5 wt. %, 0.5-10 wt. %, 0.5-7 wt. %, 0.5-5 wt. %, 0.5-2 wt. %, 0.5-1 wt. %, 1-10 wt. %, 1-7 wt. %, 1-5 wt. %, or 1-3 wt. % non-curable absorber component, based on the total weight of the build material. In some preferred embodiments, the amount of non-curable absorber component is no more than about 1 wt. %. For example, in some preferred embodiments, a build material described herein comprises 0.0001-1 wt. %, 0.0001-0.5 wt. %, 0.0001-0.1 wt. %, 0.001-1 wt. %, 0.001-0.5 wt. %, 0.001-0.1 wt. %, 0.001-0.05 wt. %, 0.01-1 wt. %, 0.01-0.5 wt. %, 0.01-0.1 wt. %, 0.01-0.05 wt. %, 0.1-1 wt. %, or 0.1-0.5 wt. % non-curable absorber component, based on the total weight of the build material. The use of a relatively small amount of non-curable absorber component, such as one of the immediately preceding amounts, can be especially advantageous for maintaining or achieving desired mechanical properties of an article formed from a given build material in a given instance, since the "inert" non-curable absorber component can play the role of a non-reactive "filler" as well as being an optically relevant material during curing. Additionally, in some embodiments, a non-curable absorber component (such as sulfonated quinoline yellow) is present in a build material in an amount sufficient to restrict penetration of the light into the build material to a depth of 30 μm or less, the light having a peak wavelength from 385 nm to 405 nm.

Build materials described herein also comprise a photoinitiator component for initiating polymerization of one or more components of the build material upon exposure to light of the proper wavelength. In some embodiments, the photoinitiator component can initiate polymerization of the acrylate component and/or one or more additional polymerizable or curable material components of the build material.

Any photoinitiator not inconsistent with the objectives of the present disclosure may be used in a build material described herein. In some embodiments, for example, the photoinitiator component comprises an alpha-cleavage type (unimolecular decomposition process) photoinitiator or a hydrogen abstraction photosensitizer-tertiary amine synergist, operable to absorb light between about 250 nm and about 400 nm, between about 250 nm and 405 nm, or between about 300 nm and about 385 nm, to yield free radical(s). Examples of alpha cleavage photoinitiators are Irgacure 184 (CAS 947-19-3), Irgacure 369 (CAS 119313-12-1), and Irgacure 819 (CAS 162881-26-7). An example of a photosensitizer-amine combination is Darocur BP (CAS 119-61-9) with diethylaminoethylmethacrylate.

In addition, in some instances, photoinitiators comprise benzoins, including benzoin, benzoin ethers, such as benzoin methyl ether, benzoin ethyl ether and benzoin isopropyl ether, benzoin phenyl ether and benzoin acetate, acetophenones, including acetophenone, 2,2-dimethoxyacetophenone and 1,1-dichloroacetophenone, benzil, benzil ketals, such as benzil dimethyl ketal and benzil diethyl ketal, anthraquinones, including 2-methylanthraquinone, 2-ethylanthraquinone, 2-tert-butylanthraquinone, 1-chloroanthraquinone and 2-amylanthraquinone, triphenylphosphine, benzoylphosphine oxides, such as 2,4,6-trimethylbenzoyldiphenylphosphine oxide (Lucirin TPO), benzophenones, such as benzophenone and 4,4'-bis(N,N'-dimethylamino) benzophenone, thioxanthones and xanthones, acridine derivatives, phenazine derivatives, quinoxaline derivatives or 1-phenyl-1,2-propanedione, 2-O-benzoyl oxime, 1-aminophenyl ketones or 1-hydroxyphenyl ketones, such as 1-hydroxycyclohexyl phenyl ketone, phenyl 1-hydroxyisopropyl ketone and 4-isopropylphenyl 1-hydroxyisopropyl ketone.

Suitable photoinitiators can also comprise photoinitiators operable for use with a HeCd laser radiation source, including acetophenones, 2,2-dialkoxybenzophenones and 1-hydroxyphenyl ketones, such as 1-hydroxycyclohexyl phenyl ketone or 2-hydroxyisopropyl phenyl ketone (=2-hydroxy-2,2-dimethylacetophenone). Additionally, in some cases, suitable photoinitiators comprise those operable for use with an Ar laser radiation source including benzil ketals, such as benzil dimethyl ketal. In some embodiments, a suitable photoinitiator comprises an α-hydroxyphenyl ketone, benzil dimethyl ketal or 2,4,6-trimethylbenzoyldiphenylphosphine oxide or a mixture thereof.

Another class of photoinitiators that may be included in a build material described herein comprises ionic dye-counter ion compounds capable of absorbing actinic radiation and generating free radicals for polymerization initiation. In some embodiments, build materials containing ionic dye-counter ion compounds can be polymerized upon exposure to visible light within the adjustable wavelength range of about 400 nm to about 700 nm. Ionic dye-counter ion compounds and their mode of operation are disclosed in EP-A-0 223 587 and U.S. Pat. Nos. 4,751,102; 4,772,530; and 4,772,541.

In some cases, a photoinitiator that may be included in a build material described herein comprises a water-soluble pyrrolidone or phosphine oxide such as a monoacylphosphine oxide (MAPO) salt or bisacylphosphine oxide (BAPO) salt, which may in some instances be a sodium or lithium MAPO or BAPO salt. In some embodiments, a photoinitiator included in a build material described herein has a structure of Formula II or Formula III:

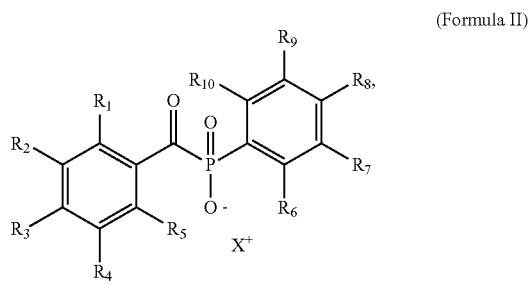

(Formula II)

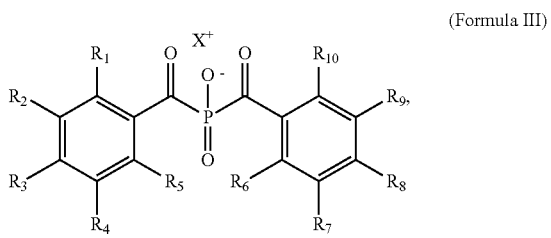

(Formula III)

wherein X is Na or Li, and wherein each of $R_1$-$R_{10}$ is independently H, $CH_3$, or $CH_2CH_3$. For example, in some preferred embodiments, each of $R_1$, $R_3$, and $R_5$ in Formula II is $CH_3$, and each of $R_2$, $R_4$, $R_6$, $R_7$, $R_8$, $R_9$, and $R_{10}$ is H. Such a species can be referred to herein as "NaP", "Na-TPO", "Sodium TPO", or "Sodium TPO-L" when X is Na, and as "LiP", "Li-TPO", "Lithium TPO", or "Lithium TPO-L" when X is Li. In other preferred embodiments, each of $R_1$, $R_3$, $R_5$, $R_6$, $R_8$, and $R_{10}$ in Formula III is $CH_3$, and each of $R_2$, $R_4$, $R_7$, and $R_9$ is H. Such a species can be referred to herein as BAPO-ONa when X is Na, and as BAPO-OLi when X is Li. It is further to be understood with reference to Formula II and Formula III above that these structures also represent resonance structures, or structures in which (for drawing convenience) the P—O single bond and the P—O double bond "switch places" in the depiction of the structure (e.g., such that the P—O double bond points "up" like the two adjacent C—O double bonds in Formula III, rather than pointing "down" as depicted above).

A photoinitiator component can be present in a build material described herein in any amount not inconsistent with the objectives of the present disclosure. In some embodiments, a photoinitiator component is present in a build material in an amount of up to about 7 wt. %, up to about 5 wt. %, up to about 3 wt. %, or up to about 2 wt. %, based on the total weight of the build material. In some cases, a photoinitiator is present in an amount of about 0.1-7 wt. %, 0.1-5 wt. %, 0.1-3 wt. %, 0.1-2 wt. %, 0.5-5 wt. %, 0.5-3 wt. %, 0.5-2 wt. %, 1-7 wt. %, 1-5 wt. %, or 1-3 wt. %, based on the total weight of the build material. In some especially preferred embodiments, a build material described herein comprises a photoinitiator component in an amount of up to about 5 wt. %. For example, in some instances, the photoinitiator component is present in the build material in an amount of 0.1-5 wt. % or 0.5-5 wt. % or, even more preferably, 1-5 wt. %, 1-3 wt. %, or 2-4 wt. %, based on the total weight of the build material.

It is further to be understood that the amounts (weight percents) described in the immediately preceding paragraph refer to photoinitiators that are non-oligomeric and non-polymeric. That is, the amounts described above refer to "monomeric" or "molecular" photoinitiators, which may, for instance, have a molecular weight of less than 400. However, it is also to be understood that oligomeric or polymeric photoinitiators may be used in build materials and methods described herein. But in such an instance (when an oligomeric or polymeric photoinitiator is used), then the amounts (weight percents) above are to be calculated without taking into account the weight of the oligomeric or polymeric portion or moiety of the oligomeric or polymeric photoinitiator. In other words, to determine the overall amount (weight percent) of the oligomeric or polymeric photoinitiator that is present in the build material, the calculation (specifically, the numerator) should be based on only the molecular weight of the photoactive moiety of the photoinitiator, not on the molecular weight(s) of the remaining moieties or repeating units of the oligomeric or polymeric photoinitiator (for purposes of the present disclosure).

Moreover, as described above, the amount of photoinitiator component and the amount of non-curable absorber component can be selected with reference to each other. For example, in some cases, a build material described herein includes up to 5 wt. % photoinitiator component and up to 1 wt. % non-curable absorber component. In other instances, a build material described herein comprises up to 4 wt. % photoinitiator component and up to 0.5 wt. % non-curable absorber component, or up to 5 wt. % photoinitiator component and up to 0.05 wt. % non-curable absorber component. In some especially preferred embodiments, a build material described herein comprises at least 1 wt. % photoinitiator component, in combination with an amount of non-curable absorber component described herein, such as an amount of up to 0.5 wt. % non-curable absorber component. As described further herein, compositions including too little photoinitiator component (especially compared to the amount of non-curable absorber component) can be insufficiently responsive to curing radiation within the distance $D_p$, with the result that insufficient polymerization takes place within the spatial region defined by $D_p$. In some cases, a preferred ratio (by weight) of photoinitiator component to non-curable absorber component is 1 or more, 5 or more, or 10 or more. In some embodiments, a preferred ratio (by weight) of photoinitiator component to non-curable absorber component is 1-200, 1-100, 5-100, 10-200, 10-150, 10-100, 25-200, 25-100, 50-200, 50-150, or 50-100 (where the weight of photoinitiator component is the numerator, and the weight of non-curable absorber component is the denominator). Such ratios can, in some cases, provide a desired curing effect (e.g., achieving a desired $D_p$, $E_c$, or $D_p/E_c$ ratio) while minimizing the amount of otherwise non-functional or non-curing "filler" material, with respect to formation of a cured polymer network.

In addition, as described above, the relative amounts of photoinitiator component and non-curable absorber component can be based, at least in part, on the total (optical) absorbance of each of the photoinitiator component and the non-curable absorber component at the wavelength λ (as opposed to being based on only weight percent or mass). For example, if a non-curable absorber component absorbs relatively weakly at the wavelength λ, then a relatively large amount (molar or weight percent) of non-curable absorber component may be needed to achieve a desired "photon competition" with the photoinitiator component, as compared to the situation when the non-curable absorber component absorbs relatively strongly at the wavelength λ (in which case a relatively small amount (molar or weight percent) of non-curable absorber component may be needed to achieve the same desired "photon competition"). Therefore, in some embodiments, a ratio of photoinitiator component to non-curable absorber component described herein (such as a weight-based ratio described above) is used when the photoinitiator component and the non-curable absorber component have absorption (or optical density) values at the wavelength λ that are within a factor of 2 of one another. Moreover, in some cases, a ratio described in the preceding paragraph (such as a ratio of photoinitiator component to non-curable absorber component within the range of 10-100) is a total optical absorbance ratio at the wavelength λ, rather than a weight-based ratio.

Turning now to other specific components of build materials described herein, build materials described herein comprise an acrylate component. Any acrylate component not inconsistent with the technical objectives of the present disclosure may be used. It is particularly to be observed that an "acrylate" component, for reference purposes herein, can comprise one or more chemical species comprising at least one acrylate, methacrylate, acrylamide, or methacrylamide moiety or functional group. Additionally, it is to be understood that the term "(meth)acrylate" includes acrylate or methacrylate or a mixture or combination thereof. Similarly, it is to be understood that the term "(meth)acrylamide" includes acrylamide or methacrylamide or a mixture or combination thereof. Thus, the term "acrylate component" refers to the totality of the foregoing species in the build material.

In some embodiments described herein, the acrylate component comprises hydrophilic (or water soluble) mono-, di-, and/or tri(meth)acrylate species. The acrylate component, for example, can comprise one or more of hydroxyalkyl(meth)acrylates (e.g., hydroxypropylacrylate), hydroxyalkyl(meth)acrylamides (e.g., N-hydroxyethylacrylamide), ethoxylated trimethylol propane triacrylate ("TAC" or trimethylolpropane ethoxylate triacrylate), acryloyl morpholine, and various combinations or mixtures thereof. In some embodiments, hydroxyalkyl(meth)acrylates include hydroxyethyl(meth)acrylate, hydroxypropyl(meth)acrylate, hydroxybutyl(meth)acrylate, and/or mixtures thereof.

The acrylate component of a build material described herein may also include a poly(ethylene glycol) diacrylate (PEGDA) component. With reference to the poly(ethylene glycol) diacrylate component as used herein, the PEGDA component can comprise a single poly(ethylene glycol) diacrylate species or multiple poly(ethylene glycol) diacrylate species of differing molecular weights.

In some embodiments, species of the PEGDA component have a weight average molecular weight of 0.1 kiloDalton (kDa) to 20 kDa or 0.2 to 20 kDa. Molecular weight of individual species of PEGDA, for example, can fall within one or more ranges set forth in Table 1.

TABLE 1

| Poly(ethylene glycol) Diacrylate Molecular Weight (kDa) |
| --- |
| 0.1-1 |
| 0.2-20 |
| 0.5-1 |
| 3-5 |
| 3-10 |
| 10-20 |
| 0.5-5 |

Any combination or mixture of poly(ethylene glycol) diacrylates of differing molecular weights is contemplated. In some embodiments, the PEGDA component comprises a mixture of two of more PEGDA species each having a weight average molecular weight from 0.5 to 5 kDa. Specific composition of the PEGDA component (when PEGDA is used) can be selected according to several considerations including, but not limited to, crosslink density, elasticity, tensile strength, and/or mesh size of the resulting hydrogel article.

It is to be understood that the acrylate component of a build material described herein can include a combination of acrylate species. For example, in some cases, the acrylate component is selected from one or more hydroxyalkyl(meth)acrylates, one or more poly(ethylene glycol) acrylates, one or more poly(ethylene glycol) diacrylates, one or more hydroxyalkyl(meth)acrylamides, or a combination of two or more of the foregoing. In certain build materials, the acrylate component can include only one hydroxyalkyl(meth)acrylate. In other build materials, the acrylate component can include a plurality (more than one) of hydroxyalkyl(meth)acrylates. In still other build materials, the acrylate component can include at least one hydroxyalkyl(meth)acrylate and at least one hydroxyalkyl(meth)acrylamide. In yet other build materials, the acrylate component can include at least one hydroxyalkyl(meth)acrylate and at least one poly(ethylene glycol) diacrylates. Thus, the present disclosure contemplates many combinations and compositions of the acrylate component that can be included in example implementations, though they are not explicitly enumerated herein.

In general, the acrylate component of a build material described herein can be present in the build material in any amount not inconsistent with the technical objectives of the present disclosure. In some embodiments, for example, the acrylate component is present in an amount or concentration of 1-90 wt. %, based on total weight of the build material. In some instances, the acrylate component is present in an amount of 1-60 wt. %, 1-40 wt. %, 10-90 wt. %, 10-80 wt. %, 10-70 wt. %, 10-60 wt. %, 10-50 wt. %, 15-90 wt. %, 15-80 wt. %, 15-75 wt. %, 15-60 wt. %, 15-50 wt. %, 15-40 wt. %, 20-90 wt. %, 20-85 wt. %, 20-70 wt. %, 20-60 wt. %, 20-50 wt. %, 30-90 wt. %, 30-80 wt. %, 30-75 wt. %, 30-60 wt. %, 30-50 wt. %, 40-90 wt. %, 40-80 wt. %, 40-70 wt. %, 40-60 wt. %, 50-90 wt. %, 50-85 wt. %, 50-75 wt. %, 50-70 wt. %, 50-60 wt. %, 60-90 wt. %, 60-80 wt. %, 60-75 wt. %, 60-70 wt. %, 70-90 wt. %, 70-85 wt. %, 70-80 wt. %, or 75-90 wt. %, based on the total weight of the build material.

Additionally, in some cases, a build material described herein comprises an acrylate component consistent with an embodiment provided in Table 2 below, where the amounts listed in Table 2 are the weight percents of the identified components, based on the total weight of the build material.

TABLE 2

| Embodiments | Acrylate Components | |
|---|---|---|
| | PEGDA Component | Water Soluble (Meth)acrylate Component |
| 1 | 0-50 wt. % | 1-60 wt. % |
| 2 | 5-30 wt. % | 5-50 wt. % |
| 3 | 5-30 wt. % | 0-60 wt. % |
| 4 | 10-20 wt. % | 5-40 wt. % |
| 5 | 5-15 wt. % | 10-60 wt. % |
| 6 | 0-10 wt. % | 20-50 wt. % |
| 7 | 5-10 wt. % | 15-55 wt. % |

Build materials described herein, in some cases, also comprise an additional curable material component, where the additional curable material component is additional to the acrylate component. Any such additional curable material component not inconsistent with the technical objectives of the present disclosure may be used. A curable material, for reference purposes herein, comprises a chemical species that includes one or more curable or polymerizable moieties. A "polymerizable moiety," for reference purposes herein, comprises a moiety that can be polymerized or cured to provide a printed 3D article or object. Such polymerizing or curing can be carried out in any manner not inconsistent with the objectives of the present disclosure. In some embodiments, for example, polymerizing or curing comprises irradiating a polymerizable or curable material with electromagnetic radiation having sufficient energy to initiate a polymerization or cross-linking reaction, or exposing the polymerizable or curable material to a reactive species that can initiate a polymerization reaction (e.g., a photoinitiator or other species that has already been "activated" to provide a reactive moiety such as a free-radical moiety). One non-limiting example of a polymerizable moiety of a curable material described herein is an ethyleneically unsaturated moiety, such as a vinyl moiety or allyl moiety. Moreover, a polymerization reaction, in some cases, comprises a free radical polymerization reaction, such as that between points of unsaturation, including points of ethyleneic unsaturation. Other polymerization reactions may also be used. As understood by one of ordinary skill in the art, a polymerization reaction used to polymerize or cure a curable material described herein can comprise a reaction of a plurality of "monomers" or chemical species having one or more functional groups or moieties that can react with one another to form one or more covalent bonds.

In general, any additional curable material or combination of additional curable materials not inconsistent with the objectives of the present disclosure may be used in a build material described herein. For example, in some cases, additional curable materials suitable for use in build materials described herein have similar wavelength absorption profiles and/or refractive indices, including absorption profiles and/or refractive indices described hereinabove with reference to the wavelength λ or wavelengths near (e.g., within 30 nm of) the wavelength λ. In some instances, the additional curable material component has a photon absorption profile that is outside of, or does not include, curing radiation having the peak wavelength λ.

In some cases, an additional curable material component comprises a compound having the structure of Formula IV or the structure of Formula V:

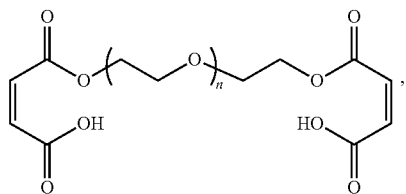
(Formula IV)

and

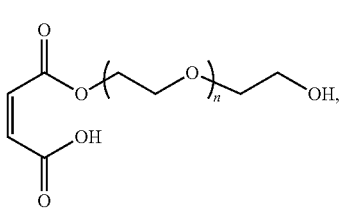
(Formula V)

wherein n is an integer between 4 and 40 or between 4 and 20. In some implementations, such a compound has the structure of Formula IV or Formula V, wherein n is an integer between 4 and 14, between 4 and 20, between 6 and 30, between 10 and 40, or between 10 and 20. Other values of n are also possible. A compound of Formula IV or Formula V can be made in any manner not inconsistent with the technical objectives of the present disclosure. For example, in some cases, a compound described herein is formed from the reaction of a poly(ethylene glycol) (PEG) and maleic anhydride (MA). A species of Formula IV can thus be referred to as "MA-PEG #-MA," where "#" is the approximate weight average molecular weight of the PEG portion of the compound. For example, "MA-PEG200-MA" refers to a compound of Formula IV wherein n has a value corresponding to a PEG moiety having a molecular weight of about 200.

An additional curable material component, if present, can be used in any amount not inconsistent with the technical objectives of the present disclosure. In some embodiments, for example, the additional curable material component can be present in an amount of 1-30 wt. %, 1-20 wt. %, 5-20 wt. %, 5-15 wt. %, 10-30 wt. %, or 10-20 wt. %, based on the total weight of the build material.

A build material described herein can also comprise water. Water can be present in any amount not inconsistent with the technical objectives of the present disclosure. For example, in some cases, water is present in the build material in an amount of 5 to 90 wt. %, 10 to 85 wt. %, 20 to 85 wt. %, or 20 to 80 wt. %, based on the total weight of the build material. In some implementations, water is present in an amount or concentration of 10-60 wt. %, 20-70 wt. %, 20-50 wt. %, 30-80 wt. %, 30-60 wt. %, 40-80 wt. %, 40-60 wt. %, 50-80 wt. %, or 50-70 wt. %, based on the total weight of the build material.

It is further to be understood that the water (or the overall build material), in some cases, can have a pH of about 1 to about 7, about 3 to about 7, or about 4 to about 6. As understood by one of ordinary skill in the art, such a pH can be obtained, for example, by in the inclusion of a Bronsted-Lowry acid or base. For instance, in some cases, a strong acid or a strong base such as hydrochloric acid or sodium hydroxide, respectively, may be included in water (or the overall build material) in a desired concentration to provide the desired pH, as understood by a person of ordinary skill. Other proton or hydroxide sources may also be used.

Build materials described herein, in some cases, can further comprise one or more photosensitizers. In general, such a sensitizer can be added to a build material to increase the effectiveness of one or more photoinitiators that may also be present. In some cases, a sensitizer comprises isopropylthioxanthone (ITX) or 2-chlorothioxanthone (CTX).

A sensitizer can be present in a build material in any amount not inconsistent with the objectives of the present disclosure. In some embodiments, a sensitizer is present in an amount ranging from about 0.1 wt. % to about 2 wt. % or from about 0.5 wt. % to about 1 wt. %, based on the total weight of the build material. However, in other cases, a build material described herein excludes a sensitizer such as described above.

Turning to another possible component of the build material described herein, build materials described herein can also comprise at least one colorant, which may be different from the non-curable absorber component of the build material. That is, in some instances, the colorant does not have the same photon absorption properties as described above for a non-curable absorber component, particularly not photon absorption properties that result in the colorant "competing" for photons with the photoinitiator and/or non-curable absorber component of the build material. Such a colorant of a build material described herein can be a particulate colorant, such as a particulate pigment, or a molecular colorant, such as a molecular dye. Any such particulate or molecular colorant not inconsistent with the objectives of the present disclosure may be used. In some cases, for instance, the colorant of a build material comprises an inorganic pigment, such as $TiO_2$ and/or ZnO. In some embodiments, the colorant of a build material comprises a colorant for use in a RGB, sRGB, CMY, CMYK, L*a*b*, or Pantone® colorization scheme. Moreover, in some cases, a particulate colorant described herein has an average particle size of less than about 5 μm, or less than about 1 μm. In some instances, a particulate colorant described herein has an average particle size of less than about 500 nm, such as an average particle size of less than about 400 nm, less than about 300 nm, less than about 250 nm, less than about 200 nm, or less than about 150 nm. In some instances, a particulate colorant has an average particle size of about 50-5000 nm, about 50-1000 nm, or about 50-500 nm.

A colorant can be present in a build material described herein in any amount not inconsistent with the technical objectives of the present disclosure. In some cases, colorant is present in the build material in an amount up to about 2 wt. %, or an amount of about 0.005-2 wt. %, 0.01-2 wt. %, 0.01-1.5 wt. %, 0.01-1 wt. %, 0.01-0.5 wt. %, 0.1-2 wt. %, 0.1-1 wt. %, 0.1-0.5 wt. %, or 0.5-1.5 wt. %, based on the total weight of the build material. In some embodiments, a build material described herein excludes colorant as described above.

Moreover, build materials described herein, in some embodiments, further comprise one or more polymerization inhibitors and/or stabilizing agents. A polymerization inhibitor can be added to a build material to provide additional thermal stability to the composition. Any polymerization inhibitor not inconsistent with the objectives of the present disclosure may be used. Moreover, a polymerization inhibitor can retard or decrease the rate of polymerization, and/or prevent polymerization from occurring for some period of time or "induction time" until the polymerization inhibitor is consumed. Further, in some cases, a polymerization inhibitor described herein is an "addition type" inhibitor. An inhibitor described herein can also be a "chain transfer type" inhibitor. In some instances, a suitable polymerization inhibitor comprises methoxyhydroquinone (MEHQ).

A stabilizing agent, in some embodiments, comprises one or more anti-oxidants. A stabilizing agent can comprise any anti-oxidant not inconsistent with the objectives of the present disclosure. In some cases, suitable anti-oxidants include various aryl compounds, including butylated hydroxytoluene (BHT), which can also be used as a polymerization inhibitor in some embodiments described herein. More generally, a single species may serve as both a stabilizing agent and a polymerization inhibitor. It is also possible, in some cases, to use a plurality of inhibitors and/or stabilizing agents, wherein differing inhibitors and/or stabilizers provide differing effects and/or work synergistically.

A polymerization inhibitor and/or a stabilizing agent can be present in a build material in any amount not inconsistent with the objectives of the present disclosure. In some embodiments, a polymerization inhibitor is present in an amount ranging from about 0.01 wt. % to about 2 wt. % or from about 0.05 wt. % to about 1 wt. %. Similarly, in some cases, a stabilizing agent is present in a build material in an amount ranging from about 0.1 wt. % to about 5 wt. %, from about 0.1 wt. % to about 2 wt. %, from about 0.5 wt. % to about 4 wt. %, or from about 1 wt. % to about 3 wt. %, based on the total weight of the build material. In some embodiments, a build material described herein excludes polymerization inhibitor and/or stabilizing agent.

Build materials described herein can have a variety of properties in a cured or uncured state, including properties related to the microstructure of the build material, which may be a complex mixture or other complex material system. In some embodiments, such structural features or other properties relate to the build material in a cured or polymerized state. A build material in a "cured" or "polymerized" state, as used throughout the present disclosure, comprises a build material that includes a curable material or polymerizable component that has been at least partially cured, i.e., at least partially polymerized and/or cross-linked. For instance, in some cases, a cured build material is at least about 70% polymerized or cross-linked or at least about 80% polymerized or cross-linked. In some embodiments, a cured build material is at least about 85%, at least about 90%, at least about 95%, at least about 98%, or at least 99% polymerized or cross-linked. In some instances, a cured build material is between about 80% and about 99% polymerized or cross-linked. The degree of polymerization or cross-linking can be determined using any protocol or method not inconsistent with the technical objectives of the present disclosure, such as by determining the percentage of monomers incorporated into the polymer network (e.g., based on molecular weight of the polymer compared to the molecular weight of the monomer, or based on the total polymer mass compared to the theoretical maximum of the total polymer mass) or by determining the amount of unincorporated monomers. When more than one method is used to determine a degree of polymerization or cross-linking, the results of the methods can be averaged to obtain a percentage described herein. It is further to be understood that the degree of polymerization or cross-linking described herein is different than "degree of polymerization" defined as the number of repeating units in a polymer molecule.

In some embodiments, a build material described herein when cured or polymerized has an elongation at break of greater than 150%, when measured according to the method of Example 18. For example, certain articles formed from polymerization of a build material in accordance with the present disclosure can have an elongation at break of 150-300%, 150-275%, 150-250%, 200-275%, or 200-250%, when measured according to the method of Example 18.

Additionally, in some embodiments, the build materials described herein, when non-cured, have a viscosity profile consistent with the requirements and parameters of one or more 3D printing systems, such as an MJP, SLA, or DLP system. For example, in some cases, a build material described herein has a dynamic viscosity at 23 or 30° C. of 1600 centipoise (cP) or less, 1200 cP or less, or 800 cP or less. In a preferred embodiment, a build material described herein has a dynamic viscosity of 500 cP or less at 23 or 30° C., when measured according to ASTM standard D2983 (e.g., using a Brookfield Model DV-II+ Viscometer). In some cases, a build material described herein when non-cured exhibits a dynamic viscosity of about 200-1600 cP, about 200-1200 cP, about 200-800 cP, about 200-500 cP, or about 200-400 cP at 23 or 30° C., when measured according to ASTM D2983.

Build materials described herein can also include, have, or exhibit any combination of components and/or properties described hereinabove individually, provided that the combination of components and/or properties is not inconsistent with the principles and technical objectives of the present invention. Moreover, in some embodiments, build materials described herein have a combination of compositional characteristics that can be especially preferred for providing improved accuracy and/or precision of additive manufacturing while also maintaining a normal (or faster) speed of the additive manufacturing process, while also maintaining (or improving) normal energy efficiency of the additive manufacturing process (in terms of energy required for curing), and/or while also maintaining (or improving) desired mechanical properties of the printed articles. It is to be understood that "normal" or "maintained" characteristics as described above are relative to build materials that are comparable to inventive build materials according to the present disclosure/preferred embodiments, but that do not fall within the inventive metrics identified above. Similarly, it is further to be understood that "desired mechanical properties" can vary based on a given selection of build material components. Again, however, build materials such as the preferred build materials described herein can provide the advantages contemplated in this disclosure without substantial loss of mechanical properties the build materials would otherwise provide if they (the build materials) fell outside of the inventive parameters described herein. For example, a build material that is formulated to have high elongation (e.g., through selection of a specific acrylate component or other component) can maintain such elongation despite the inclusion of a photoinitiator component and non-curable absorbable component in the formulation in a manner consistent with the preferred embodiments above (e.g., an elongation can be achieved with preferred build materials described herein, wherein the elongation deviates by no greater than 5% from the desired elongation, using the desired value as the denominator for calculating the percent deviation).

Build materials described herein can be produced in any manner not inconsistent with the objectives of the present disclosure. In some embodiments, for instance, a method for the preparation of a build material described herein comprises the steps of mixing the components of the build material, optionally melting the mixture, and filtering the (optionally molten) mixture. In some cases, the components are mixed and optionally melted at a temperature between about 25° C. and about 35° C., or at a temperature in the range of 25-55° C., 35-65° C., or 45-75° C. In some instances in which it is desirable or necessary to melt one or more solid components of the build material, mixing and/or melting can be carried about a temperature in a range from about 75° C. to about 85° C. In some embodiments, a build material described herein is produced by placing all components of the build material in a reaction vessel, optionally heating the resulting mixture, and stirring the resulting mixture at a temperature between about 25° C. and about 75° C. or a temperature ranging from about 75° C. to about 85° C. The stirring (and optionally the heating) are continued until the mixture attains a substantially homogenized liquid (or molten) state. In general, the liquid (or molten) mixture can be filtered while in a flowable state to remove any large undesirable particles that may interfere with jetting or extrusion or other printing process. The filtered mixture can then be cooled to ambient temperatures (if cooling is needed) and stored until ready for use in a 3D printing system.

II. Methods of Forming a 3D Article

In another aspect, methods of forming or "printing" a 3D article or object by additive manufacturing are described herein. Methods of forming a 3D article or object described herein can include forming the 3D article from a plurality of layers of a build material described herein in a layer-by-layer manner. Methods of forming a 3D article by additive manufacturing can also include forming the object in a manner other than a layer-by-layer manner. Any build material described hereinabove in Section I may be used in a method described herein.

For example, in some cases, a method described herein comprises providing a build material having a penetration depth ($D_p$) and a critical energy ($E_c$) at a wavelength λ; and selectively curing a portion of the build material using incident curing radiation having a Gaussian distribution of wavelengths and a peak wavelength at the wavelength λ, wherein the build material has a $D_p$ greater than 200 μm and less than 300 μm, and an $E_c$ of 3-12 mJ/cm². Additionally, in some such cases, the build material has a ratio of $D_p$ to $E_c$, in units of (μm cm²)/mJ, of greater than 10 or greater than 15. In some embodiments, the build material used in a method described herein has a ratio of $D_p$ to $E_c$, in units of (μm cm²)/mJ, between 15 and 100, between 15 and 50, between 15 and 25, or between 20 and 50. In other instances, the $D_p$ of the build material used in a method described herein is greater than 10 μm and less than 50 μm, and the $E_c$ of the build material is 5-40 mJ/cm² or 10-40 mJ/cm². Further, in some such instances, the build material has a ratio of $D_p$ to $E_c$, in units of (μm cm²)/mJ, of less than 3, less than 2, or less than 1, such as a ratio between 0.2 and 2, or between 0.5 and 1.5. In still other instances, the $D_p$ of the build material used in a method described herein is greater than 25 μm and less than 50 μm, and the $E_c$ of the build material is 5-30 mJ/cm² or 5-10 mJ/cm². Further, in some such instances, the build material has a ratio of $D_p$ to $E_c$, in units of (μm cm²)/mJ, of less than 10, such as a ratio between 2 and 6, or between 3 and 5. Moreover, in some embodiments described herein, the build material is selectively cured according to preselected computer aided design (CAD) parameters, and the $D_p$ corresponds to a voxel depth of the CAD parameters. Moreover, in some cases, one or more layers of a build material described herein has a thickness of about 10 μm to about 100 μm, about 10 μm to about 80 μm, about 10 μm to about 50 μm, about 10 μm to about 40 μm, about 20 μm to about 100 μm, about 20 μm to about 80 μm, or about 20 μm to about 40 μm. Other thicknesses are also possible.

Further, in some embodiments, a method described herein can provide high resolution printing, including of hydrogel articles. In some cases, for example, a hydrogel article printed by a method described herein comprises one or more features having overgrowth less than 20 percent or less than 10 percent relative to computer dimensions of the features. Overgrowth can be measured in any desired direction and/or plane, including the x-y plane, x-z plane, and/or y-z plane. Direction of overgrowth measurement can be determined by nature of the structural feature of the printed hydrogel article.

Performing a printing process described herein can provide a printed 3D article from a build material described herein that has a high feature resolution. The "feature resolution" of an article, for reference purposes herein, can be the smallest controllable physical feature size of the article or the pixel or voxel size of the printing process, where it is understood that "pixel" and "voxel" refer to the CAD parameter or model of the article. In some embodiments, a printed article described herein has an average voxel size greater than 50 μm per side on average (e.g., when the average voxel size corresponds to a volume having an average length in all three dimensions of 50-100 μm, 50-75 μm, 60-100 μm, 60-80 μm, or 60-70 μm). In other cases, a printed article described herein has an average voxel size of less than 50 μm, less than 40 μm, less than 30 μm, or less than 20 μm per side on average (e.g., when the average voxel size corresponds to a volume having an average length in all three dimensions of 10-45 μm, 10-40 μm, 10-30 μm, 10-25 μm, 10-20 μm, 15-45 μm, or 15-40 μm).

Additionally, it is to be understood that methods of printing a 3D article described herein can include, for example, MJP, DLP, or SLA 3D printing methods. For example, in some instances, a MJP method of printing a 3D article comprises selectively depositing layers of a build material described herein in a fluid state onto a substrate, such as a build pad of a 3D printing system. In addition, in some embodiments, a method described herein further comprises supporting at least one of the layers of the build material with a support material. Any support material not inconsistent with the objectives of the present disclosure may be used.

A method described herein can also comprise curing the layers of the build material, including with curing radiation described above (such as curing radiation having a peak wavelength λ). Moreover, curing can comprise polymerizing one or more polymerizable moieties or functional groups of one or more components of the build material. In some cases, a layer of deposited build material is cured prior to the deposition of another or adjacent layer of build material. Additionally, curing one or more layers of deposited build material, in some embodiments, is carried out by exposing the one or more layers to electromagnetic radiation, such as UV light, visible light, or infrared light, as described above.

Further details regarding various methods, including "material deposition" methods (such as MJP) or "vat polymerization" methods (such as SLA), are provided below.

A. Material Deposition Methods

In a material deposition method, one or more layers of a build material described herein are selectively deposited onto a substrate and cured. Curing of the build material may occur after selective deposition of one layer, each layer, several layers, or all layers of the build material.

In some instances, a build material described herein is selectively deposited in a fluid state onto a substrate, such as a build pad of a 3D printing system. Selective deposition may include, for example, depositing the build material according to preselected CAD parameters. For example, in some embodiments, a CAD file drawing corresponding to a desired 3D article to be printed is generated and sliced into a sufficient number of horizontal slices. Then, the build material is selectively deposited, layer by layer, according to the horizontal slices of the CAD file drawing to print the desired 3D article. A "sufficient" number of horizontal slices is the number necessary for successful printing of the desired 3D article, e.g., to produce it accurately and precisely.

Further, in some embodiments, a preselected amount of build material described herein is heated to the appropriate temperature and jetted through a print head or a plurality of print heads of a suitable inkjet printer to form a layer on a print pad in a print chamber. In some cases, each layer of build material is deposited according to preselected CAD parameters. A suitable print head to deposit the build material, in some embodiments, is a piezoelectric print head. Additional suitable print heads for the deposition of build material and support material described herein are commercially available from a variety of ink jet printing apparatus manufacturers. For example, Xerox, Hewlett Packard, or Ricoh print heads may be used in some instances.

Additionally, in some embodiments, a build material described herein remains substantially fluid upon deposition. Alternatively, in other instances, the build material exhibits a phase change upon deposition and/or solidifies upon deposition. Moreover, in some cases, the temperature of the printing environment can be controlled so that the jetted droplets of build material solidify on contact with the receiving surface. In other embodiments, the jetted droplets of build material do not solidify on contact with the receiving surface, remaining in a substantially fluid state. Additionally, in some instances, after each layer is deposited, the deposited material is planarized and cured with electromagnetic (e.g., UV, visible, or infrared light) radiation prior to the deposition of the next layer. Optionally, several layers can be deposited before planarization and curing, or multiple layers can be deposited and cured followed by one or more layers being deposited and then planarized without curing. Planarization corrects the thickness of one or more layers prior to curing the material by evening the dispensed material to remove excess material and create a uniformly smooth exposed or flat up-facing surface on the support platform of the printer. In some embodiments, planarization is accomplished with a wiper device, such as a roller, which may be counter-rotating in one or more printing directions but not counter-rotating in one or more other printing directions. In some cases, the wiper device comprises a roller and a wiper that removes excess material from the roller. Further, in some instances, the wiper device is heated. It should be noted that the consistency of the jetted build material described herein prior to curing, in some embodiments, should desirably be sufficient to retain its shape and not be subject to excessive viscous drag from the planarizer.

Moreover, a support material, when used, can be deposited in a manner consistent with that described hereinabove for the build material. The support material, for example, can be deposited according to the preselected CAD parameters such that the support material is adjacent or continuous with one or more layers of the build material. Jetted droplets of the support material, in some embodiments, solidify or freeze on contact with the receiving surface. In some cases, the deposited support material is also subjected to planarization, curing, or planarization and curing. Any support material not inconsistent with the objectives of the present disclosure may be used.

Layered deposition of the build material and support material can be repeated until the 3D article has been formed. In some embodiments, a method of printing a 3D article further comprises removing the support material from the build material.

Curing of the build material may occur after selective deposition of one layer of build material, of each layer of build material, of several layers of build material, or of all layers of the build material necessary to print the desired 3D article. In some embodiments, a partial curing of the deposited build material is performed after selective deposition of one layer of build material, each layer of build material, several layers of build material, or all layers of the build material necessary to print the desired 3D article. A "partially cured" build material, for reference purposes herein, is one that can undergo further curing. For example, a partially cured build material is up to about 30% polymerized or cross-linked or up to about 50% polymerized or cross-linked. In some embodiments, a partially cured build material is up to about 60%, up to about 70%, up to about 80%, up to about 90%, or up to about 95% polymerized or cross-linked.

Partial curing of the deposited build material can include irradiating the build material with an electromagnetic radiation source or photocuring the build material (including with curing radiation described hereinabove). Any electromagnetic radiation source not inconsistent with the objectives of the present disclosure may be used, e.g., an electromagnetic radiation source that emits UV, visible or infrared light. For example, in some embodiments, the electromagnetic radiation source can be one that emits light having a wavelength from about 300 nm to about 900 nm, e.g., a Xe arc lamp.

Further, in some embodiments, a post-curing is performed after partially curing is performed. For example, in some cases, post-curing is carried out after selectively depositing all layers of the build material necessary to form a desired 3D article, after partially curing all layers of the build material, or after both of the foregoing steps have been performed. Moreover, in some embodiments, post-curing comprises photocuring, including with curing radiation described hereinabove having a peak wavelength $\lambda$. Again, any electromagnetic radiation source not inconsistent with the objectives of the present disclosure may be used for a post-curing step described herein. For example, in some embodiments, the electromagnetic radiation source can be a light source that has a higher energy, a lower energy, or the same energy as the electromagnetic radiation source used for partial curing. In some cases wherein the electromagnetic radiation source used for post-curing has a higher energy (i.e., a shorter wavelength) than that used for partial curing, a Xe arc lamp can be used for partial curing and a Hg lamp can be used for post-curing.

Additionally, after post-curing, in some cases, the deposited layers of build material are at least about 80% polymerized or cross-linked or at least about 85% polymerized or cross-linked. In some embodiments, the deposited layers of build material are at least about 90%, at least about 95%, at least about 98%, or at least about 99% polymerized or cross-linked. In some instances, the deposited layers of build material are about 80-100%, about 80-99%, about 80-95%, about 85-100%, about 85-99%, about 85-95%, about 90-100%, or about 90-99% polymerized or cross-linked.

B. Vat Polymerization Methods

It is also possible to form a 3D article from a build material described herein using a vat polymerization method, such as an SLA method. Thus, in some cases, a method of printing a 3D article described herein comprises retaining a build material described herein in a fluid state in a container and selectively applying energy (particularly, for instance, the curing radiation having the peak wavelength $\lambda$) to the build material in the container to solidify at least a portion of a fluid layer of the build material, thereby forming a solidified layer that defines a cross-section of the 3D article. Additionally, a method described herein can further comprise raising or lowering the solidified layer of build material to provide a new or second fluid layer of unsolidified build material at the surface of the fluid build material in the container, followed by again selectively applying energy (e.g., the curing radiation) to the build material in the container to solidify at least a portion of the new or second fluid layer of the build material to form a second solidified layer that defines a second cross-section of the 3D article. Further, the first and second cross-sections of the 3D article can be bonded or adhered to one another in the z-direction (or build direction corresponding to the direction of raising or lowering recited above) by the application of the energy for solidifying the build material. Moreover, in some instances, the electromagnetic radiation has an average wavelength of 300-900 nm, and in other embodiments the electromagnetic radiation has an average wavelength that is less than 300 nm. In some cases, the curing radiation is provided by a computer controlled laser beam or other light source. In addition, in some cases, raising or lowering a solidified layer of build material is carried out using an elevator platform disposed in the container of fluid build material. A method described herein can also comprise planarizing a new layer of fluid build material provided by raising or lowering an elevator platform. Such planarization can be carried out, in some cases, by a wiper or roller.

It is further to be understood that the foregoing process can be repeated a desired number of times to provide the 3D article. For example, in some cases, this process can be repeated "n" number of times, wherein n can be up to about 100,000, up to about 50,000, up to about 10,000, up to about 5000, up to about 1000, or up to about 500. Thus, in some embodiments, a method of printing a 3D article described herein can comprise selectively applying energy (e.g., curing radiation of peak wavelength $\lambda$) to a build material in a container to solidify at least a portion of an nth fluid layer of the build material, thereby forming an nth solidified layer that defines an nth cross-section of the 3D article, raising or lowering the nth solidified layer of build material to provide an (n+1)th layer of unsolidified build material at the surface of the fluid build material in the container, selectively applying energy to the (n+1)th layer of build material in the container to solidify at least a portion of the (n+1)th layer of the build material to form an (n+1)th solidified layer that defines an (n+1)th cross-section of the 3D article, raising or lowering the (n+1)th solidified layer of build material to provide an (n+2)th layer of unsolidified build material at the surface of the fluid build material in the container, and continuing to repeat the foregoing steps to form the 3D article. Further, it is to be understood that one or more steps of a method described herein, such as a step of selectively applying energy (e.g., curing radiation described herein) to a layer of build material, can be carried out according to an image of the 3D article in a computer-readable format. General methods of 3D printing using stereolithography are further described, inter alia, in U.S. Pat. Nos. 5,904,889 and 6,558,606.

In a vat polymerization method such as described above, the build material may be partially cured as described in Section IIA above. For example, in some embodiments, selectively applying energy to the build material in the container to solidify at least a portion of a fluid layer of the build material may include partially curing at least a portion of a fluid layer of the build material. In other embodiments, partial curing of at least a portion of a fluid layer of the build material may occur after a first layer of the build material is provided and solidified, before or after a second layer of the build material is provided or solidified, or before or after one, several, or all subsequent layers of the build material are provided or solidified.

Additionally, in some embodiments of a vat polymerization method described herein, after partial curing or after the desired 3D article is formed, post-curing as described in Section IIA above may be performed. The desired 3D article may be, for example, an article that corresponds to the design in a CAD file.

C. Additional Features of Methods

In some embodiments of methods described herein in Section IIA or Section IIB, the method further comprise leaching a non-curable absorber component (e.g., a sulfonated quinoline yellow) from the printed three-dimensional hydrogel article produced by the method, following completion of the print job. The hydrogel article, for example, can be placed in a water bath or other water or aqueous-based environment prior to use as an implant or other biomedical device or scaffold. Notably, leaching of the non-curable absorber component (e.g., the sulfonated quinoline yellow) from the printed article does not acidify the surrounding water environment. The water bath or other surrounding water environment comprising the leached non-curable absorber component (e.g., the sulfonated quinoline yellow) can exhibit a pH of 6.5 to 8 in the absence of buffer or other pH control species added to the water. In some embodiments, the pH of the water environment containing the leached non-curable absorber component (e.g., the sulfonated quinoline yellow) can have a pH of 7-7.5. This marks a fundamental departure from other hydrogel inks, which can produce highly acidic aqueous environments upon leaching of components subsequent to article completion.

III. Printed 3D Articles

In another aspect, printed 3D articles are described herein. In some embodiments, a printed 3D article is formed from a build material described herein. Any build material described hereinabove in Section I may be used. For example, in some cases, the build material comprises 1-90 wt. % acrylate component, 0.5-3 wt. % photoinitiator component, 0.1-1 wt. % non-curable absorber component, and 10-85 wt. % water, based on the total weight of the build material (wherein the total amount of the foregoing components is equal to 100 wt. %), and wherein the photoinitiator component is operable to initiate curing of the acrylate component when the photoinitiator component is exposed to incident curing radiation having a Gaussian distribution of wavelengths and a peak wavelength λ, wherein the build material has a penetration depth ($D_p$) and a critical energy ($E_c$) at the wavelength λ, wherein the $D_p$ is greater than 200 μm and less than 300 μm. and wherein the $E_c$ is 3-12 mJ/cm$^2$, or wherein the build material has a $D_p$ of 10-50 μm and an $E_c$ of 5-40 mJ/cm$^2$.

Hydrogel articles printed according to methods described herein can find application in a variety of fields, including the medical field. The hydrogel articles, for example, can be medical implants. The hydrogel medical implants can be employed for tissue regeneration and/or serve as scaffolds for cellular seeding and/or growth.

EXAMPLES

Some embodiments of build materials for 3D printing are also further illustrated in the following non-limiting Examples.

Examples 1-4

Some specific embodiments of build materials are provided in Table 3 below. The amounts in Table 3 refer to the wt. % of each component of the identified composition, based on the total weight of the composition. Additionally, "SQY" stands for "sulfonated quinoline yellow" and "PI" stands for "photoinitiator." Moreover, in all cases in Table 3 below, water provides the balance of components to reach 100 wt. %. In Examples 1-4, the "PEGDA Components" have a weight average molecular weight of 3000-7000; and the "Other Acrylate Components" comprise monofunctional and multifunctional alkoxylated acrylate and hydroxyalkylacrylate. It should further be noted that, as described above, the "PEGDA Components" and "Other Acrylate Components" below can together also be described as a single "acrylate component."

TABLE 3

| | Composition Components | | | |
|---|---|---|---|---|
| Example | PEGDA Component | Other Acrylate Component | SQY | PI |
| 1 | 4-6 | 10-15 | 0.2-0.4 | 1-3 |
| 2 | 4-6 | 9-13 | 0.3-0.5 | 1.5-2.5 |
| 3 | 4-6 | 8-12 | 0.2-0.3 | 1-2 |
| 4 | 4-6 | 8-12 | 0.1-0.2 | 1-2 |

Examples 5-10

Table 4 provides formulations of build materials according to some embodiments described herein. In Table 4, "Ex." means "Example," and the amounts listed for a given Example are weight percents, based on the total weight of the composition of that Example. It is to be understood that all components of a given Example composition add up to 100 weight percent. Table 5 provides components of Examples 5-10. Table 6 provides the $D_p$ and $E_c$ values for Examples 5-10. Additionally, in Table 5, "SQY" refers to sulfonated quinoline yellow. All components of Examples 5-10 below, other than the photoinitiator component and non-curable absorber component, were substantially non-absorbing at the wavelength λ, such that these species were essentially optical spectators, as described hereinabove.

TABLE 4

| | Example Compositions | | | | | |
|---|---|---|---|---|---|---|
| Component | Ex. 5 | Ex. 6 | Ex. 7 | Ex. 8 | Ex. 9 | Ex. 10 |
| Acrylate Component | 39.5 | 39.5 | 39.5 | 39.5 | 39.5 | 39.5 |
| Additional Curable Component | 11.8 | 11.8 | 11.8 | 11.8 | 11.8 | 11.8 |
| Non-Curable Absorber Component | 0.325 | 0.35 | 0.35 | 0.33 | 0.4 | 0.4 |
| Photoinitiator Component | 1.8 | 1.5 | 1.6 | 1.7 | 1.7 | 1.5 |
| Water | Balance | Balance | Balance | Balance | Balance | Balance |

TABLE 5

| Component | Ex. 5 | Ex. 6 | Ex. 7 | Ex. 8 | Ex. 9 | Ex. 10 |
|---|---|---|---|---|---|---|
| Acrylate Component | HEAA (N-hydroxy ethyl acrylamide) + HPA (hydroxy propyl acrylate) + HBA (hydroxy butyl acrylate) | HEAA + HPA + HBA | HEAA + HPA + HBA | HEAA + HPA + HBA | HEAA + HPA + HBA | HEAA + HPA + HBA |
| Additional Curable Component | MA-PEG200-MA | MA-PEG200-MA | MA-PEG200-MA | MA-PEG200-MA | MA-PEG200-MA | MA-PEG200-MA |
| Non-Curable Absorber Component | SQY | SQY | SQY | SQY | SQY | SQY |
| Photoinitiator Component | Sodium TPO-L | Sodium TPO-L | Sodium TPO-L | Sodium TPO-L | Sodium TPO-L | Sodium TPO-L |

TABLE 6

$D_p$ and $E_c$

| | Ex. 5 | Ex. 6 | Ex. 7 | Ex. 8 | Ex. 9 | Ex. 10 |
|---|---|---|---|---|---|---|
| Dp (μm) | 36.4 | 51.0 | 49.9 | 47.9 | 29.3 | 27.6 |
| $E_c$ (mJ/cm$^2$) | 7.2 | 26.3 | 25.1 | 10.5 | 5.4 | 8.0 |
| Dp/Ec (μm cm$^2$/mJ) | 5.1 | 1.9 | 2.0 | 4.6 | 5.4 | 3.5 |

Examples 11-17

Table 7 provides formulations of build materials according to some embodiments described herein. In Table 7, "Ex." means "Example," and the amounts listed for a given Example are weight percents, based on the total weight of the composition of that Example. Dashes (--) indicate a component was absent (zero weight percent). It is to be understood that all components of a given Example composition add up to 100 weight percent. Table 8 provides components of Examples 11-17. In Table 8, "PEGDA X" refers to a PEGDA having an average weight average molecular weight of "X" (e.g., PEGDA 3400 have a weight average molecular weight of 3400). Additionally, in Table 8, "SQY" refers to sulfonated quinoline yellow, and "tart." refers to tartrazine. NaP refers to Sodium TPO-L, and LiP refers to Lithium TPO-L. Table 9 provides the $D_p$ and $E_c$ values for Examples 11-17. All components of Examples 11-17 below, other than the photoinitiator component and non-curable absorber component, were substantially non-absorbing at the wavelength λ, such that these species were essentially optical spectators, as described hereinabove.

TABLE 7

Example Compositions

| Component | Ex. 11 | Ex. 12 | Ex. 13 | Ex. 14 | Ex. 15 | Ex. 16 | Ex. 17 |
|---|---|---|---|---|---|---|---|
| Acrylate Component | 55 | 33 | 24 | 45 | 32 | 60 | 65 |
| Additional Curable Component | — | — | — | — | — | — | — |
| Non-Curable Absorber Component | 0.3 | 0.2 | 0.5 | 0.5 | 1 | 0.5 | 1 |
| Photoinitiator Component | 1.5 | 1.1 | 1 | 1 | 1 | 1 | 1 |
| Water | Balance | Balance | Balance | Balance | Balance | Balance | Balance |

TABLE 8

Components

| Component | Ex. 11 | Ex. 12 | Ex. 13 | Ex. 14 | Ex. 15 | Ex. 16 | Ex. 17 |
|---|---|---|---|---|---|---|---|
| Acrylate Component | PEGDA 3400 + PEGDA 600 + HPA + | PEGDA 3400 + PEGDA 600 + HPA + | PEGDA 3400 + HPA + TAC | PEGDA 3400 + PEGDA 600 + HPA + | PEGDA 3400 + PEGDA 600 + HPA + | PEGDA 10k + HPA + HBA + TAC | PEGDA 3400 + PEGDA 600 + HPA + |

TABLE 8-continued

| | Components | | | | | | |
|---|---|---|---|---|---|---|---|
| Component | Ex. 11 | Ex. 12 | Ex. 13 | Ex. 14 | Ex. 15 | Ex. 16 | Ex. 17 |
| | HBA + TAC | HBA + TAC | | HBA + TAC | TAC | | TAC |
| Additional Curable Component | — | — | — | — | — | — | — |
| Non-Curable Absorber Component | UV386A | UV386A | UV386A | tart. | tart. | SQY | SQY |
| Photoinitiator Component | NaP | NaP | NaP | NaP | NaP | NaP | LiP |

TABLE 9

| | $D_p$ and $E_c$ | | | | | | |
|---|---|---|---|---|---|---|---|
| | Ex. 11 | Ex. 12 | Ex. 13 | Ex. 14 | Ex. 15 | Ex. 16 | Ex. 17 |
| Dp (μm) | 23.75 | 17.46 | 10.70 | 63.15 | 14.98 | 24.51 | 16.81 |
| $E_c$ (mJ/cm²) | 21.97 | 13.56 | 36.92 | 34.56 | 28.64 | 20.85 | 17.98 |
| Dp/Ec (μm cm²/mJ) | 1.08 | 1.29 | 0.29 | 1.83 | 0.52 | 1.18 | 0.93 |

Example 18

Tensile testing of printed articles for determining elongation at break was carried out as follows. The test formulation (the ink, build material, or polymerizable liquid) was printed at room temperature (approximately 23-25° C.) into horizontally oriented rings in 20 μm thick layers on a digital light processing (DLP) printer. The rings had a necked region with a defined 1 mm by 1 mm square cross section. The rings were taken off the printer platform and rinsed of uncured material (e.g., by placing the rings in phosphate buffered saline (PBS) or water at room temperature for 10 minutes or less). Then the rings were loaded onto a dynamic mechanical analysis (DMA) system and vertically stretched at 100% strain per minute (at room temperature) until the instrument reached a maximum strain or the sample broke, thereby providing the Elongation at Break (EOB). By finding the slope of the first 10% strain, the modulus is found.

Some additional, non-limiting example embodiments are provided below.

Embodiment 1. A build material for hydrogel article formation comprising:
an acrylate component;
a photoinitiator component;
a non-curable absorber component; and
water,
wherein the photoinitiator component is operable to initiate curing of the acrylate component when the photoinitiator component is exposed to incident curing radiation having a Gaussian distribution of wavelengths and a peak wavelength λ;
wherein the build material has a penetration depth ($D_p$) and a critical energy ($E_c$) at the wavelength λ;
wherein the $D_p$ is greater than 200 μm and less than 300 μm; and
wherein the $E_c$ is 3-12 mJ/cm².

Embodiment 2. The build material of Embodiment 1, wherein the build material has a ratio of $D_p$ to $E_c$, in units of (μm cm²)/mJ, of greater than 10 or greater than 15.

Embodiment 3. The build material of Embodiment 1, wherein the build material has a ratio of $D_p$ to $E_c$, in units of (μm cm²)/mJ, between 15 and 100, between 15 and 50, between 15 and 25, or between 20 and 50.

Embodiment 4. A build material for hydrogel article formation comprising:
an acrylate component;
a photoinitiator component;
a non-curable absorber component; and
water,
wherein the photoinitiator component is operable to initiate curing of the acrylate component when the photoinitiator component is exposed to incident curing radiation having a Gaussian distribution of wavelengths and a peak wavelength λ;
wherein the build material has a penetration depth ($D_p$) and a critical energy ($E_c$) at the wavelength λ;
wherein the $D_p$ is greater than 10 μm and less than 50 μm; and
wherein the $E_c$ is 5-40 mJ/cm² or 10-40 mJ/cm².

Embodiment 5. The build material of Embodiment 4, wherein the build material has a ratio of $D_p$ to $E_c$, in units of (μm cm²)/mJ, of 0.2 to 2.

Embodiment 6. A build material for hydrogel article formation comprising:
an acrylate component;
a photoinitiator component;
a non-curable absorber component; and
water,
wherein the photoinitiator component is operable to initiate curing of the acrylate component when the photoinitiator component is exposed to incident curing radiation having a Gaussian distribution of wavelengths and a peak wavelength λ;
wherein the build material has a penetration depth ($D_p$) and a critical energy ($E_c$) at the wavelength λ;
wherein the $D_p$ is greater than 25 μm and less than 50 μm; and wherein the $E_c$ is 5-30 mJ/cm² or 5-10 mJ/cm².

Embodiment 7. The build material of Embodiment 6, wherein the build material has a ratio of $D_p$ to $E_c$, in units of (μm cm²)/mJ, of less than 10.

Embodiment 8. The build material of Embodiment 6, wherein the build material has a ratio of $D_p$ to $E_c$, in units of (μm cm$^2$)/mJ, between 2 and 6 or between 3 and 5.

Embodiment 9. The build material of any of the preceding Embodiments, wherein:
the acrylate component is present in the build material in an amount of 1-90 wt. %, 1-60 wt. %, 1-40 wt. %, 10-90 wt. %, 10-80 wt. %, 10-70 wt. %, 10-60 wt. %, 10-50 wt. %, 15-90 wt. %, 15-80 wt. %, 15-75 wt. %, 15-60 wt. %, 15-50 wt. %, 15-40 wt. %, 20-90 wt. %, 20-85 wt. %, 20-70 wt. %, 20-60 wt. %, 20-50 wt. %, 30-90 wt. %, 30-80 wt. %, 30-75 wt. %, 30-60 wt. %, 30-50 wt. %, 40-90 wt. %, 40-80 wt. %, 40-70 wt. %, 40-60 wt. %, 50-90 wt. %, 50-85 wt. %, 50-75 wt. %, 50-70 wt. %, 50-60 wt. %, 60-90 wt. %, 60-80 wt. %, 60-75 wt. %, 60-70 wt. %, 70-90 wt. %, 70-85 wt. %, 70-80 wt. %, or 75-90 wt. %, based on the total weight of the build material;
the photoinitiator component is present in the build material in an amount of 0.1-5 wt. %, 0.1-3 wt. %, 0.1-2 wt. %, or 0.5-2 wt. %, based on the total weight of the build material;
the non-curable absorber component is present in the build material in an amount of 0.1-5 wt. %, 0.1-3 wt. %, 0.1-2 wt. %, 0.1-1 wt. %, or 0.1-0.5 wt. %, based on the total weight of the build material; and
the water is present in the build material in an amount of 10-85 wt. % or 20-80 wt. %, based on the total weight of the build material.

Embodiment 10. The build material of any of the preceding Embodiments, wherein the acrylate component comprises one or more poly(ethylene glycol) diacrylate (PEGDA) species.

Embodiment 11. The build material of Embodiment 9, wherein the acrylate component comprises a plurality of differing PEGDA species having differing molecular weight.

Embodiment 12. The build material of Embodiment 10 or Embodiment 11, wherein the one or more PEGDA species has a weight average molecular weight of 0.1 kDa to 20 kDa.

Embodiment 13. The build material of any of the preceding Embodiments, wherein the acrylate component comprises one or more hydroxyalkylacrylates.

Embodiment 14. The build material of any of the preceding Embodiments, wherein:
the build material comprises 0.5-2 wt. % photoinitiator component and 0.1 to 1 wt. % non-curable absorber component; and
the ratio of photoinitiator component to non-curable absorber component, by weight, is between 2 and 10 or between 5 and 100.

Embodiment 15. The build material of any of the preceding Embodiments, wherein both the non-curable absorber component and the photoinitiator component have an absorption peak within 30 nm of the wavelength λ.

Embodiment 16. The build material of any of the preceding Embodiments, wherein the total absorbance of the non-curable absorber component at the wavelength λ is about 0.1 to 10 times the total absorbance of the photoinitiator component at the wavelength λ.

Embodiment 17. The build material of any of the preceding Embodiments, wherein the non-curable absorber component comprises a water-soluble yellow dye.

Embodiment 18. The build material of any of the preceding Embodiments, wherein the non-curable absorber component comprises a quinoline yellow.

Embodiment 19. The build material of any of the preceding Embodiments, wherein the non-curable absorber component comprises a sulfonated quinoline yellow.

Embodiment 20. The build material of Embodiment 19, wherein the sulfonated quinoline yellow comprises at least one of monosulfonate, disulfonate and trisulfonate species.

Embodiment 21. The build material of Embodiment 4, wherein:
the acrylate component comprises 0-50 wt. % PEGDA species; the PEGDA species has a weight average molecular weight of 200 to 20,000 Da;
the acrylate component comprises 0-60 wt. % hydrophilic or water soluble acrylate;
the photoinitiator component is present in an amount of 0.1-3 wt. %;
the non-curable absorber component is present in an amount of 0.1-3 wt. %; and
the water is present in an amount of 5-90 wt. %.

Embodiment 22. The build material of Embodiment 21, wherein the acrylate component comprises 5-30 wt. % PEGDA species.

Embodiment 23. The build material of Embodiment 21 or Embodiment 22, wherein the acrylate component comprises 5-50 wt. % water soluble acrylate.

Embodiment 24. The build material of Embodiment 21, Embodiment 22, or Embodiment 23, wherein the photoinitiator component is present in an amount of 0.5-2 wt. %.

Embodiment 25. The build material of Embodiment 21, Embodiment 22, Embodiment 23, or Embodiment 24, wherein the non-curable absorber component is present in an amount of 0.1-1 wt. %.

Embodiment 26. The build material of Embodiment 21, Embodiment 22, Embodiment 23, Embodiment 24, or Embodiment 25, wherein the water is present in an amount of 20-80 wt. %.

Embodiment 27. The build material of Embodiment 21, Embodiment 22, Embodiment 23, Embodiment 24, Embodiment 25, or Embodiment 26, wherein:
the hydrophilic or water soluble acrylate comprises one or more hydroxylalkyl(meth)acrylates; and
the non-curable absorber component comprises UV386A, SQY, or tartrazine.

Embodiment 28. A method of forming a three-dimensional article by additive manufacturing, the method comprising:
providing the build material of any of Embodiments 1-27; and
selectively curing a portion of the build material using incident curing radiation having a Gaussian distribution of wavelengths and a peak wavelength at the wavelength λ.

Embodiment 29. The method of Embodiment 28, wherein:
the build material is selectively cured according to preselected computer aided design (CAD) parameters; and
the $D_p$ corresponds to a voxel depth of the CAD parameters.

Embodiment 30. The method of Embodiment 29, wherein the voxel depth is 50 μm or less, 30 μm or less, or 25 μm or less.

Embodiment 31. The method of Embodiment 29, wherein the voxel depth is 50 μm or more.

Embodiment 32. The method of any of Embodiments 28-31, wherein providing the build material comprises selectively depositing layers of the build material in a fluid state onto a substrate to form the three-dimensional article.

Embodiment 33. The method of any of Embodiments 28-31, wherein:
provinding the build material comprises retaining the build material in a fluid state in a container;
selectively curing a portion of the build material comprises selectively applying the curing radiation to the build material in the container to solidify at least a portion of a first fluid layer of the build material, thereby forming a first solidified layer that defines a first cross-section of the article;
raising or lowering the first solidified layer to provide a second fluid layer of the build material at a surface of the fluid build material in the container; and
selectively applying the curing radiation to the build material in the container to solidify at least a portion of the second fluid layer of the build material, thereby forming a second solidified layer that defines a second cross-section of the article, the first cross-section and the second cross-section being bonded to one another in a z-direction.

Embodiment 34. The method of any of Embodiments 28-33, wherein:
the non-curable absorber component is present in the build material in an amount to restrict penetration of the incident curing radiation into one or more layers of the build material to a depth of 30 μm or less; and
λ is from 385 nm to 405 nm.

Embodiment 35. A printed three-dimensional article formed from the build material of any of Embodiments 1-27 and/or using the method of any of Embodiments 28-34.

Embodiment 36. The article of Embodiment 35, wherein the article is a medical implant.

Embodiment 37. The article of Embodiment 35, wherein the article is a tissue graft scaffold, a hydrogel capsule for delivery of a therapeutic species to a biological environment, a microfluidic organ on a chip, a nerve graft, or a regenerative organ or tissue scaffold.

Embodiment 38. A build material for hydrogel article formation comprising:
a poly(ethylene glycol) diacrylate component;
sulfonated quinoline yellow;
a photoinitiator component; and
water.

Embodiment 39. The build material of Embodiment 38, wherein the poly(ethylene glycol) diacrylate component comprises poly(ethylene glycol) diacrylate species of differing molecular weight.

Embodiment 40. The build material of Embodiment 39, wherein the poly(ethylene glycol) diacrylate species can have molecular weights ranging from 0.1 kDa to 20 kDa.

Embodiment 41. The build material of Embodiment 38, wherein the poly(ethylene glycol) diacrylate component is present in an amount of 1-60 wt. % based on total weight of the build material.

Embodiment 42. The build material of Embodiment 38, wherein the sulfonated quinoline yellow is present in an amount of 0.1-5 wt. % based on total weight of the build material.

Embodiment 43. The build material of Embodiment 38, wherein the sulfonated quinoline yellow is present in an amount of 0.1-1 wt. % based on total weight of the build material.

Embodiment 44. The build material of Embodiment 38, wherein the sulfonated quinoline yellow comprises at least one of monosulfonate, disulfonate and trisulfonate species.

Embodiment 45. The build material of Embodiment 38 further comprising an acrylate component.

Embodiment 46. The build material of Embodiment 45, wherein the acrylate component comprises one or more hydroxyalkylacrylates.

Embodiment 47. The build material of Embodiment 46, wherein the acrylate component is present in an amount of 1-40 wt. % based on total weight of the build material.

Embodiment 48. The build material of Embodiment 38, wherein the photoinitiator component is present in an amount of 0.1-5 weight percent based on total weight of the build material.

Embodiment 49. A method of printing a three-dimensional hydrogel article comprising: providing the build material of any of Embodiments 38-48; and printing and curing the build material with light to form the hydrogel article.

Embodiment 50. The method of Embodiment 49, wherein the build material is provided in a layer-by-layer process.

Embodiment 51. The method of Embodiment 49, wherein the polyethylene glycol diacrylate component comprises poly(ethylene glycol) diacrylate species of differing molecular weight.

Embodiment 52. The method of Embodiment 49, wherein the hydrogel article comprises one or more features having overgrowth less than 20 percent relative to computer dimensions of the features.

Embodiment 53. The method of Embodiment 49 further comprising leaching sulfonated quinoline yellow from the hydrogel article into a water bath.

Embodiment 54. The method of Embodiment 53, wherein pH of the water bath comprising leached sulfonated quinoline yellow is in a range of 6.5 to 8.

Embodiment 55. The method of Embodiment 49, wherein the hydrogel article is a medical implant.

All patent documents referred to herein are incorporated by reference in their entireties. Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed:

1. A build material for hydrogel article formation comprising:
an acrylate component;
a photoinitiator component;
a non-curable absorber component; and
water,
wherein the photoinitiator component is operable to initiate curing of the acrylate component when the photoinitiator component is exposed to incident curing radiation having a Gaussian distribution of wavelengths and a peak wavelength λ;
wherein the build material has a penetration depth ($D_p$) and a critical energy ($E_c$) at the wavelength λ;
wherein the $D_p$ is greater than 10 μm and less than 50 μm; and
wherein the $E_c$ is 5-40 mJ/cm$^2$.

2. The build material of claim 1, wherein the build material has a ratio of $D_p$ to $E_c$, in units of (μm cm$^2$)/mJ, of less than 3.

3. The build material of claim 1, wherein the build material has a ratio of $D_p$ to $E_c$, in units of (μm cm$^2$)/mJ, between 0.2 and 2.

4. The build material of claim 1, wherein:
the acrylate component is present in the build material in an amount of 5-80 wt. %, based on total weight of the build material;
the photoinitiator component is present in the build material in an amount of 0.1-3 wt. %, based on the total weight of the build material;
the non-curable absorber component is present in the build material in an amount of 0.1-1 wt. %, based on the total weight of the build material; and
the water is present in the build material in an amount of 10-85 wt. %, based on the total weight of the build material.

5. The build material of claim 1, wherein the acrylate component comprises one or more poly(ethylene glycol) diacrylate (PEGDA) species.

6. The build material of claim 5, wherein the acrylate comprises a plurality of differing PEGDA species having differing molecular weight.

7. The build material of claim 5, wherein the one or more PEGDA species has a weight average molecular weight of 0.1 kDa to 20 kDa.

8. The build material of claim 1, wherein the acrylate component comprises one or more hydroxyalkylacrylates.

9. The build material of claim 1, wherein:
the build material comprises 0.5-2 wt. % photoinitiator component and 0.1 to 1 wt. % non-curable absorber component; and
the ratio of photoinitiator component to non-curable absorber component, by weight, is between 2 and 10.

10. The build material of claim 1, wherein both the non-curable absorber component and the photoinitiator component have an absorption peak within 30 nm of the wavelength $\lambda$.

11. The build material of claim 1, wherein the total absorbance of the non-curable absorber component at the wavelength $\lambda$ is about 0.1 to 10 times the total absorbance of the photoinitiator component at the wavelength $\lambda$.

12. The build material of claim 1, wherein the non-curable absorber component comprises a water-soluble yellow dye.

13. The build material of claim 1, wherein the non-curable absorber component comprises a quinoline yellow or a sulfonated quinoline yellow.

14. A method of forming a three-dimensional article by additive manufacturing, the method comprising:
providing the build material of claim 1; and
selectively curing a portion of the build material using incident curing radiation having a Gaussian distribution of wavelengths and a peak wavelength at the wavelength $\lambda$.

15. The method of claim 14, wherein:
the build material is selectively cured according to preselected computer aided design (CAD) parameters;
the $D_p$ corresponds to a voxel depth of the CAD parameters; and
the voxel depth is 50 µm or less.

16. The method of claim 14, wherein providing the build material comprises selectively depositing layers of the build material in a fluid state onto a substrate to form the three-dimensional article.

17. The method of claim 14, wherein:
providing the build material comprises retaining the build material in a fluid state in a container;
selectively curing a portion of the build material comprises selectively applying the curing radiation to the build material in the container to solidify at least a portion of a first fluid layer of the build material, thereby forming a first solidified layer that defines a first cross-section of the article;
raising or lowering the first solidified layer to provide a second fluid layer of the build material at a surface of the fluid build material in the container; and
selectively applying the curing radiation to the build material in the container to solidify at least a portion of the second fluid layer of the build material, thereby forming a second solidified layer that defines a second cross-section of the article, the first cross-section and the second cross-section being bonded to one another in a z-direction.

18. The method of claim 14, wherein:
the non-curable absorber component is present in the build material in an amount to restrict penetration of the incident curing radiation into one or more layers of the build material to a depth of 30 µm or less; and
$\lambda$ is from 385 nm to 405 nm.

19. A printed three-dimensional article formed from the build material of claim 1.

20. The article of claim 19, wherein the article is a medical implant.

* * * * *